(12) United States Patent
Sullenger et al.

(10) Patent No.: US 8,790,924 B2
(45) Date of Patent: Jul. 29, 2014

(54) REVERSIBLE PLATELET INHIBITION

(75) Inventors: Bruce A. Sullenger, Durham, NC (US);
Shahid Nimjee, Durham, NC (US);
Sabah Oney, Palo Alto, CA (US);
Nanette Que-Gewirth, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/296,045

(22) Filed: Nov. 14, 2011

(65) Prior Publication Data

US 2012/0264815 A1    Oct. 18, 2012

Related U.S. Application Data

(63) Continuation-in-part of application No. 12/311,943, filed as application No. PCT/US2007/022358 on Oct. 19, 2007.

(60) Provisional application No. 60/852,650, filed on Oct. 19, 2006.

(51) Int. Cl.
*C12N 15/113*   (2010.01)
*C12N 15/90*    (2006.01)
*C07H 21/04*    (2006.01)

(52) U.S. Cl.
USPC .......... 435/375; 514/44 R; 435/325; 424/93.2; 424/93.21

(58) Field of Classification Search
CPC .............................................. C12N 2310/317
USPC ........ 435/13, 325, 372, 375; 424/93.21, 93.7; 514/44 R, 13.8
See application file for complete search history.

(56) References Cited

U.S. PATENT DOCUMENTS

| | | | | |
|---|---|---|---|---|
| 5,660,985 | A | * | 8/1997 | Pieken et al. ................ 435/6.11 |
| 5,770,198 | A | * | 6/1998 | Coller et al. ............... 424/153.1 |
| 7,566,701 | B2 | * | 7/2009 | Diener et al. ............... 514/44 R |
| 2003/0083294 | A1 | * | 5/2003 | Sullenger et al. ............... 514/44 |
| 2006/0193821 | A1 | * | 8/2006 | Diener et al. ............... 424/78.37 |

OTHER PUBLICATIONS

International Search Report for PCT/US2007/022358 mailed Aug. 18, 2008.
Written Opinion for PCT/US2007/022358 mailed Aug. 18, 2008.
Oney et al, "Antidote-controlled platelet inhibition targeting von Willebrand factor with aptamers", Oligonucleotides 17(3):265-274 (2007)—Abstract.

* cited by examiner

*Primary Examiner* — Janet Epps-Smith
(74) *Attorney, Agent, or Firm* — Andrus Intellectual Property Law, LLP

(57) ABSTRACT

The present invention relates, in general, to receptors and to platelet aggregation and, in particular, to a method of inhibiting platelet aggregation using an aptamer that binds to and inhibits the activity of a receptor, such as glycoprotein IIb/IIIa (gpIIb/IIIa), and to aptamers suitable for use in such a method. The invention also relates to antidotes to antiplatelet agents and to methods of using such antidotes to reverse aptamer-induced platelet inhibition. The invention further relates to von Willebrand Factor (VWF) inhibitors, and antidotes therefore, and to methods of using same.

6 Claims, 18 Drawing Sheets

| | |
|---|---|
| N40 of CI-6 | 5'-UUCAACGCUGUGAAGGGCUUAUACGAGCGGAUUACCC-3' |
| AO1 | 3'-AAGUUGCGACACUUCCCGAA-5' |
| AO2 | 3'-UGCGACACUUCCCGAAUAUG-5' |
| AO3 | 3'-ACACUUCCCGAAUAUGCUCG-5' |
| AO4 | 3'-UUCCCGAAUAUGCUCGCCUA-5 |
| AO5 | 3'-CGAAUAUGCUCGCCUAAUGGG-5' |

Binding improved over consecutive rounds of VWF selection.

VWF R9.14 vs AOs

Antidote Sel 2 3'W1 reverses VWF R9.14 activity in a PFA-100

Figure 8

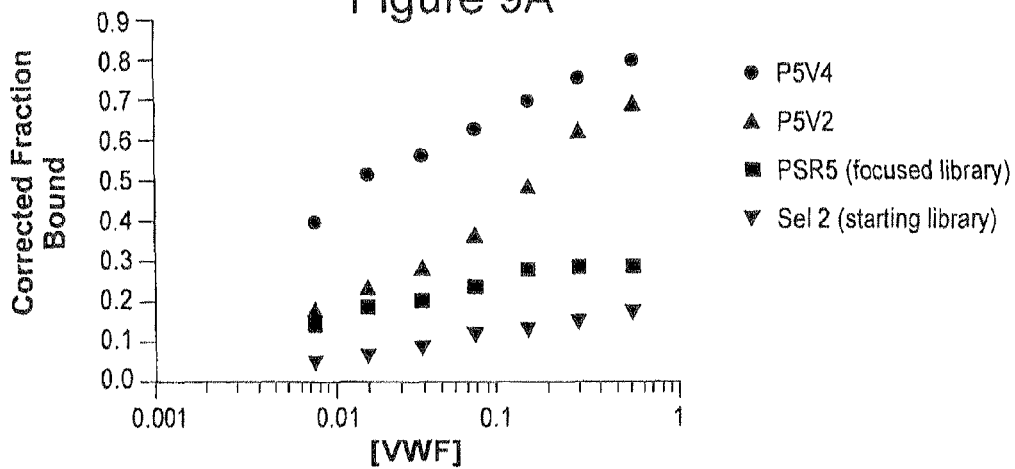
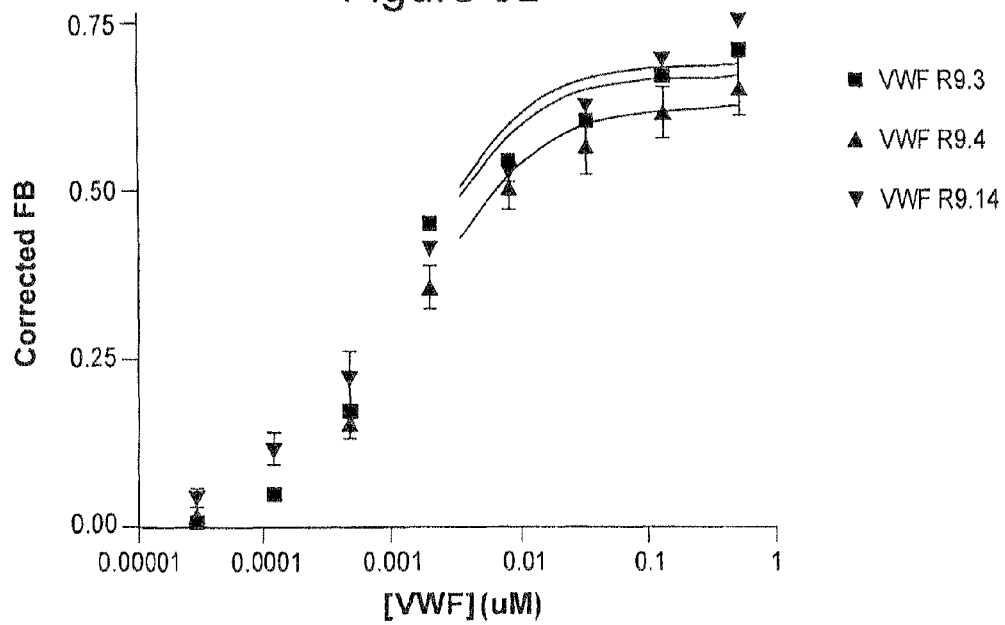
Convergent systematic evolution of ligands by exponential enrichment (SELEX) yielded aptamers that bind to von Willebrand factor (VWF) with high affinity.

Figure 9C

|  | VWF | VWF SPI | VWF SPIII |
|---|---|---|---|
| R9.3 | ● | | ● |
| R9.4 | ● | ● | ● |
| R9.14 | ● | | ● |

Figure 9D

SP III fragment

SP I fragment

N — D' D3 — A1 A2 — A3 D4 — B1-3 — C1 C2 — C

- D' D3: FVIII, Heparin
- A1: GP Ibα, Collagen, Ristocetin
- A3: Collagen
- C1: GP IIbIIIa Convergent systematic evolution of ligands by exponential enrichment (SELEX) yielded aptamers that bind to von Willebrand factor (VWF) with high affinity.

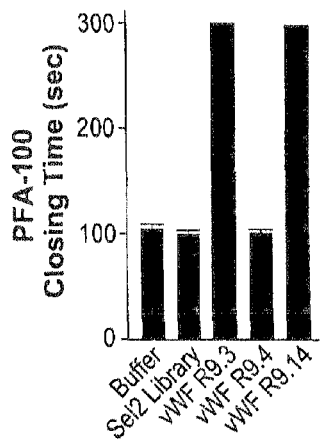
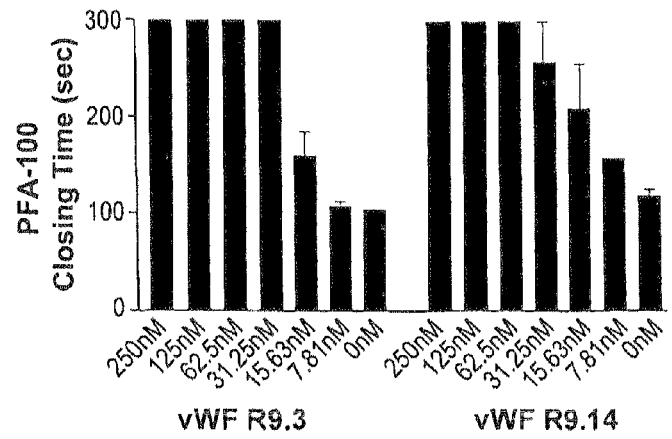
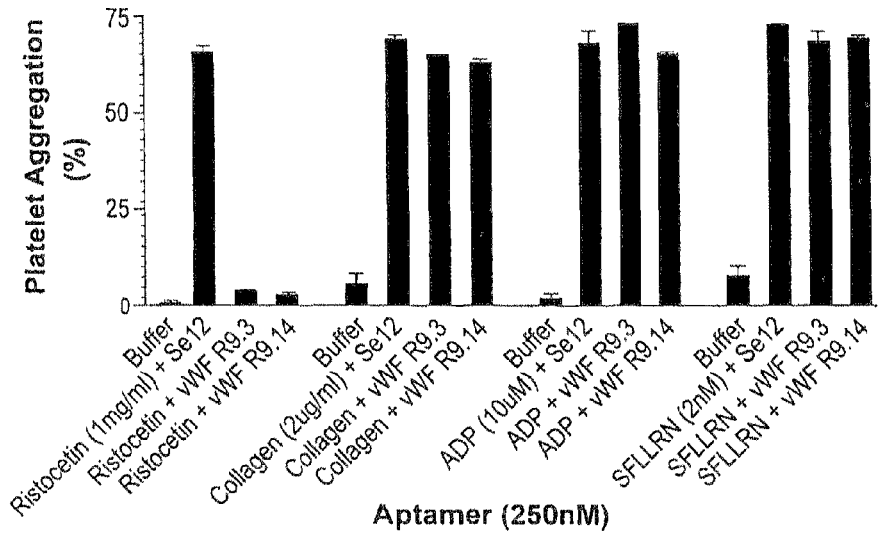
von Willebrand factor (VWF) aptamers R9.3 and R9.14 inhibit platelet aggregation by blocking the VWF–GP Ib-IX-V interaction.

Antidote oligonucleotides to aptamer von Willebrand factor (VWF) R9.14 can reverse aptamer function rapidly and for a prolonged period of time.

Antidote oligonucleotides to aptamer von Willebrand factor (VWF) R9.14 can reverse aptamer function r

SEQUENCE LISTING

```
<160> NUMBER OF SEQ ID NOS: 74

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tatagaccac agcctgagta ttaaccacca acccaggtac t                         41
```

```
<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tataaccgtt ctagcgctaa tgacactata gcatcccgt                          40

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgccacatgc ctcagataca gcacgcacct tcgacctaat                         40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
acctgctagc agtggcgcga ataaaccatc gcagcatcaa                         40

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggacttgcga gccagtccac acgccgcgac taaagagact tctc                    44

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acagatctac ccgagacaaa catcccaccc tccga                              35

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tcctaagatt aaatacgcca cggctcactt acacaccag                          39

<210> SEQ ID NO 8
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgccacatgc ctcagataca gcacgcacct tcgacctaat                               40

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcccttggat gagactaaca acctaccaca tcctatactc                               40

<210> SEQ ID NO 10
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gggaggacga tgcggtggac gaactgccct cagctacttt catgttgctg acgcacagac         60
gactcgctga ggatcc                                                        76

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
cuuaagcagg agagcgcgau                                                    20

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
agcugcuuaa gcaggagagc                                                    20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uugauagcug cuuaagcagg                                                    20
```

```
<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gcuauuugau agcugcuuaa                                                       20

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aagaugggcu auuugauagc ug                                                    22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tctcggatcc tcagcgagtc gtct                                                  24

<210> SEQ ID NO 17
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(55)
<223> OTHER INFORMATION: a, c, t, g, unknown or other

<400> SEQUENCE: 17
gggaggacga tgcggnnnnn nnnnnnnnnn nnnnnnnnnn nnnnnnnnnn nnnnncagac           60
gactcgctga ggatcc                                                           76

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
atcgcgctct cctgcttaag cagctatcaa atagcccact                                 40

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 19
tatagaccac agcctgagat taaccaccaa cccaggact                              39

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgctccttgg ccttagccct ggaaccatca atcctcttcg                             40

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tggacgaact gccctcagct actttcatgt tgctgacgca                             40

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t, g, unknown or other
<220> FEATURE:
<221> NAME/KEY: modified_base
<222> LOCATION: (8)..(8)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other

<400> SEQUENCE: 22
acgngtanac ctgctacaat ancagcctaa atggcccact                             40

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atccctgcca aacatacttt cgctttggct aggactccct                             40

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcaccccctc gacaacgacc ctgtgcccct cgatcgacca                              40

<210> SEQ ID NO 25
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cccattacgg cttccttgta ttcttggaca agccgcgact                              40

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acccttgaca acaacccttc ctcaccaacc cctcccaac                               39

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ataccctcga caacgaccct attcgcatga cacctctgtg                              40

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atgaatcctc ctgtcgaaca acagctgttt cagcccaact                              40

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gaccgactga ttcgcaccag accacgacgt tatggcccaa                              40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gtcgacttag ccccgtgctc ggcgcttcac agtcgactat                              40

<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgagatcaca ctgccccaat agccactgaa ctagcgcgca                           40

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
accattcgcg agcacaacgc tttgtactca acactccacg                           40

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
accgttcaga aatgacccca cgcacatcca tccctgagct                           40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acgtgatcct cggacccagc attgcattat atgcgcccct                           40

<210> SEQ ID NO 35
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
actctcagcc catgtgcctc aaccaaggca cggcttgctc                           40

<210> SEQ ID NO 36
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cacccttcac ccgaaccctg cccacgaccc cacacccgc                            40

<210> SEQ ID NO 37
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atgaccagcc cctcgacaac gaccctgctg gctcaaccgt t                             41

<210> SEQ ID NO 38
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (22)..(24)
<223> OTHER INFORMATION: a, c, t, g, unknown or other
<220> FEATURE:
<221> NAME/KEY: modified_base
<222> LOCATION: (33)..(33)
<223> OTHER INFORMATION: a, c, t, g, unknown or other

<400> SEQUENCE: 38
gaccgccgcn nccgacccna gnnntgctgt gtncgctccg cc                            42

<210> SEQ ID NO 39
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uucaacgcug ugaagggcuu auacgagcgg auuaccc                                  37

<210> SEQ ID NO 40
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aagcccuuca cagcguugaa                                                     20

<210> SEQ ID NO 41
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
guauaagccc uucacagcgu                                                     20

<210> SEQ ID NO 42
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
gcucguauaa gcccuucaca                                                     20

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
auccgcucgu auaagcccuu                                                     20

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
ggguaauccg cucguauaag c                                                   21

<210> SEQ ID NO 45
<211> LENGTH: 76
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
gggaggacga ugcgguggac gaacugcccu cagcuacuuu caguugcug acgcacagac          60 gacucgcuga ggaucc                                                         76

<210> SEQ ID NO 46
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gggaggacga tgcggtggac gaactgccct cagctacttt catgttgctg acgcacagac          60
gactcgctga ggatccgaga                                                      80

<210> SEQ ID NO 47
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gggaggacga tgcggtggac gaactgccct cagctacttt catgttgctg acgcacagac      60
gactcgctga ggatccg      77

<210> SEQ ID NO 48
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gggaggacga tgcggtggac gaactgccct cagctacttt catgttgctg acgcacagac      60
gactcgctga gg      72

<210> SEQ ID NO 49
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gggaggacga tgcggtggac gaactgccct cagctacttt catgttgctg acgcacagac      60
gactcgctg      69

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gggaggcctc agctactttc atgttgctga cgcacagacg actcgctgag g      51

<210> SEQ ID NO 51
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gggaggacga tgcggtggac gaactgccct cagctacttt catgttgctg acgcacagac      60
gactcg      66

<210> SEQ ID NO 52
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gggaggacga tgcggtggac gaactgccct cagctacttt catgttgctg acgcacagac      60
agc      63

<210> SEQ ID NO 53
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gggaggacga tgcggtggac gaactgccct cagctacttt catgttgctg acgcacaga        59

<210> SEQ ID NO 54
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gggaggatgc ggtggacgaa ctgccctcag ctactttcat gttgctgacg cacagacgac        60
tcgctg                                                                  66

<210> SEQ ID NO 55
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gggaggcggt ggacgaactg ccctcagcta ctttcatgtt gctgacgcac agacgactcg        60
ctg                                                                     63

<210> SEQ ID NO 56
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggaggtgga cgaactgccc tcagctactt tcatgttgct gacgcacaga cgactcgctg        60

<210> SEQ ID NO 57
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gggaggadga actgccctca gctactttca tgttgctgac gcacagacga ctcgctg          57

<210> SEQ ID NO 58
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
gggaggaact gccctcagct actttcatgt tgctgacgca cagacgactc gctg    54

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gggaggtgcc ctcagctact ttcatgttgc tgacgcacag acgactcgct g    51

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gggaggtcag ctactttcat gttgctga    28

<210> SEQ ID NO 61
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gggaggtgga cgaactgccc tcagctacca tgttgctgac gcacagacga ctcgctg    57

<210> SEQ ID NO 62
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gggaggtgga cgaactgccc tcagctacgt tgctgacgca cagacgactc gctg    54

<210> SEQ ID NO 63
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggaggtgga cgaactgccc tacgcacaga cgactcgctg    40

<210> SEQ ID NO 64
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gggaggtgga cgaactgccc tctactttca tgttgctgac gcacagacga ctcgctg    57

<210> SEQ ID NO 65
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gggaggtgga cgaactgccc tctttcatgt tgctgacgca cagacgactc gctg    54

<210> SEQ ID NO 66
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gggaggtgga cgaactgccc tctactttca tgttgacgca cagacgactc gctg    54

<210> SEQ ID NO 67
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
gggaggugga cgaacugccc ucagcuacuu ucauguugcu gacgcacaga cgacucgcug    60
t    61

<210> SEQ ID NO 68
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gttcgtccac ctccc    15

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gagggcagtt cgtcca    16

<210> SEQ ID NO 70
<211> LENGTH: 16
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 70
aagtagctga gggcag                                                         16

<210> SEQ ID NO 71
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
aacatgaaag tagctg                                                         16

<210> SEQ ID NO 72
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
ctgtgcgtca acatga                                                         16

<210> SEQ ID NO 73
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
agtcgtctgt gcgtca                                                         16

<210> SEQ ID NO 74
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
cagcgagtcg tctgtg                                                         16
```

REVERSIBLE PLATELET INHIBITION

This is a continuation-in-part of U.S. application Ser. No. 12/311,943, filed Mar. 31, 2010, which is the U.S. national phase of International Application No. PCT/US2007/022358, filed Oct. 19, 2007, which designated the U.S. and claims priority from Provisional Application No. 60/852,650, filed Oct. 19, 2006, the entire contents of which applications are incorporated herein by reference.

This invention was made with government support under Grant No. NHLB1 RO1 HL65222 awarded by the National Institutes of Health. The government has certain rights in the invention.

TECHNICAL FIELD

The present invention relates, in general, to receptors and to platelet aggregation and, in particular, to a method of inhibiting platelet aggregation using an aptamer that binds to and inhibits the activity of a receptor, such as glycoprotein IIb/IIIa (gpIIb/IIIa), and to aptamers suitable for use in such a method. The invention also relates to antidotes to antiplatelet agents and to methods of using such antidotes to reverse aptamer-induced platelet inhibition. The invention further relates to von Willebrand Factor (VWF) inhibitors, and antidotes therefore, and to methods of using same.

BACKGROUND

Inhibitors of gpIIb/IIIa have proven to be efficacious as anti-thrombotic agents for use in treatment of cardiovascular disease. Abciximab, a chimeric human-murine monoclonal antibody, was the first gpIIb/IIIa antagonist developed (Binkley et al, Nucleic Acid Research 23:3198-3205 (1995)). Eptifibatide, a small peptide, and Tirofiban, a small non-peptide, both interact with and inhibit the function of the beta-3 ($\beta_3$) sub-unit of gpIIb/IIIa (Scarborough et al, J. Biol. Chem. 268:1066-1073 (1993), Bednar et al, J. Pharmacol. Exp. Ther. 285:1317-1326 (1998), Hartman et al, J. Med. Chem. 35:4640-4642 (1992)). The two main drugs used clinically are Abciximab and Eptifibatide.

Abciximab is approved for use in patients undergoing percutaneous coronary intervention (PCI) and is being studied for use in acute coronary syndromes (ACS). The EPIC trial revealed that Abciximab reduced the morbidity and mortality of cardiovascular disease, but also showed an increase in major bleeding episodes from 7% to 14% and an increase in blood transfusions from 10% to 21% (Lincoff et al, Am. J. Cardiol. 79:286-291 (1997)). Eptifibitide is also used in PCI and, like Abciximab, is an effective antithrombotic with a trend towards increased bleeding (The PURSUIT Trial Investigators, N. Eng. J. Med. 339:436-443 (1998)). In addition to bleeding complications, readministration is a potential concern, especially with Abciximab, where initial administration was associated with a human antichimeric antibody response in 7% of patients (Tcheng, Am. Heart J. 139:S38-45 (2000)). Finally, thrombocytopenia is also seen in patients who receive gpIIb/IIIa antagonists. Severe thrombocytopenia (<20,000/μl) occurs in almost 0.5% of patients after intravenous administration (Topol et al, Lancet 353:227-231 (1999)). The most pressing issue with these drugs, given the clinical environment in which they are used, is the need to turn off or reverse their activity quickly. This would allow physicians to reduce the side effects of the medications should they become a risk to the health and safety of the patient and would also allow surgeons to perform immediate coronary bypass graft surgery, should the need arise. Thus, the development of new gpIIb/IIIa inhibitors with matched antidotes is a medical priority.

Ribonucleic acid ligands, or aptamers, are a new class of drug compounds ideally suited to anticoagulation therapy. They bind to their targets with high affinity and specificity, are only slightly immunogenic and their bioavailability can be tailored to suit a particular clinical need (Nimjee et al, Annu. Rev. Med. 56:555-583 (2005)). More recently, research has shown that these drugs can be controlled with antidotes both in vitro and in vivo (Nimjee et al, Molecular Therapy: the Journal of the American Society of Gene Therapy (2006), Mol. Ther. 14:408-45 Epub Jun. 9, 2006, Rusconi et al, Nat. Biotechnol. 22:1423-1428 (2004), Rusconi et al, Nature 419: 90-94 (2002)).

The present invention relates to RNA ligands (aptamers) that inhibit receptor function and activity, including platelet function and activity. The invention further relates to specific, rationally-designed antidotes that can reverse this inhibitory effect.

SUMMARY OF THE INVENTION

In general, the present invention relates to inhibitors of platelet aggregation. More specifically, the invention relates to RNA ligands or aptamers that can inhibit the activity of a receptor, such as gpIIb/IIIa, as well as aptamers that inhibit VWF, and to methods of using same. The invention additionally relates to agents (antidotes) that can reverse the inhibitory effect of such ligands/aptamers.

Objects and advantages of the present invention will be clear from the description that follows.

BRIEF DESCRIPTION OF THE DRAWINGS

FIG. 5A. Antidote oligonucleotides (SEQ ID NOs:40-44, respectively, in order of appearance) were designed to portions of the variable region of CI-6 (SEQ ID NO:39). FIG. 5B. Modified (2'-Omethyl) antidote oligonucleotides (AO) designed against distinct regions of the aptamer. AO2 represented the most effective inhibitor with a closing time of 81±19.5 s, while AO5 was the least effective, with a closing time of 129.5±14.5 s; error bars represent S.E.M.

FIG. 8. Antidote Sel 2 3'W1 reverses VWF R9.14 activity in a PFA-100: VWF aptamer R9.14 was added to 800 microL whole blood at 40 nM concentration, incubated for 5 minutes. Than, the antidote added at 50× molar excess. After an additional 5 minute incubation, a PFA-100 assay was performed to determine if the antidote reversed the VWF R9.14 aptamer activity. @95C columns are positive control. VWF R9.14 T7 is a mutant aptamer used as negative control. Each point has been performed in duplicate. Error bars represent the range of data.

FIGS. 9A-9D. "Convergent" SELEX yielded aptamers that bind to VWF with high affinity. FIG. 9A) Progress of the "convergent" SELEX was followed using a nitrocellulose filter binding assay. Inverted triangles (▼) represent the starting RNA library (Sel2). Squares (■) represent the plasma focused library. Triangles (▲) represent "convergent" SELEX round 2 and diamonds (♦) represent "convergent" SELEX round 4. The X-axis represents VWF concentration and the Y-axis represents the fraction of RNA bound to the protein. FIG. 9B) Binding affinities of VWF aptamers R9.3, R9.4 and R9.14 were determined using a nitrocellulose filter binding assay. Squares (■) represent R9.3, triangles (▲) represent R9.4 and inverted triangles (▼) represent R9.14. Each data point was done in triplicate; error bars represent the SEM (standard error of the mean) of the data. FIG. 9C) Binding of aptamers to VWF, VWF SPI and VWF SPIII fragments was determined using a nitrocellulose filter binding assay. Aptamers R9.3 and R9.14 bind to both full length VWF and the VWF SPIII fragment but not to the VWF SPI fragment. Aptamer R9.4 binds to full length VWF, the VWF SPIII and the VWF SPI fragment. FIG. 9D) Cartoon depicting the VWF, its subunits and SP I and SP III fragments.

FIGS. 10A-10C. VWF aptamers R9.3 and R9.14 inhibit platelet aggregation by blocking the VWF-GP Ib-IX-V interaction. FIG. 10A) The function of VWF aptamers R9.3, R9.4 and R9.14 was measured at a 1 µM concentration in a PFA-100 assay. Platelet buffer and starting aptamer library (Sel2) were used as negative controls. Error bars represent the range of data. Each data point was done in triplicate. FIG. 10B) Varying concentrations of VWF aptamers R9.3 and R9.14 were added to normal whole blood; closing times were measured in a PFA-100 assay using collagen/ADP cartridges. Error bars represent the range of data. Each data point was done in triplicate. FIG. 10C) VWF aptamers R9.3 and VWF R9.14 were tested in ristocetin, collagen, ADP and thrombin (SFLLRN) induced platelet aggregation. Filled bars represent percent aggregation in normal platelet rich plasma. Error bars represent the range of data; each data point was done in triplicate.

FIG. 11A) Cartoon depicting the antidote design to aptamer VWF R9.14 (SEQ ID NO:45). Black bars depict the positions of sequence complementarities. FIG. 11B) Reversal of aptamer VWF R9.14 binding to VWF was accomplished by antidote oligonucleotide 6 (AO6) (triangles) but not by AO5 (inverted triangles). AO6 and AO5 together (diamonds) also inhibit aptamer binding to VWF. The starting library (Sel2; circles) was used as a control.

FIG. 12A) AO6 completely reverses aptamer function in a PFA-100 assay (black bars) at a 40:1 ratio. A scrambled antidote oligonucleotide is used as a negative control (grey bars). Error bars represent the range of data. Each data point was done in triplicate. FIG. 12B) AO6 achieved complete reversal of aptamer VWF R9.14 function in a PFA-100 assay in 2 minutes. AO6 was used at 40:1 ratio to VWF R9.14 (40 nM). Error bars represent the range of data. Each data point was done in triplicate. FIG. 12C) AO6 inhibits aptamer VWF R9.14 function for 4 hours in a PFA-100 assay (black bars). A scrambled antidote oligonucleotide was used as a negative control (grey bars). Error bars represent the range of data. Each data point was done in triplicate.

FIG. 13A: VWF Aptamer truncate 9.14-T10 binds with similar affinity compared to full length aptamer. Binding was performed using a nitrocellulose-filter binding assay. Circles (●) represent full-length aptamer VWF. 9.14. Squares (■) represent aptamer VWF 9.14-T10. The X-axis represents VWF concentration and the Y-axis represents the fraction of RNA bound to the protein. FIG. 13B: VWF Aptamer 9.14 and derivatives inhibit platelet activity in a PFA-100 assay. The inhibitory activities of VWF aptamers 9.14, 9.14-T10 and Ch-9.14-T10 were measured at a 50 nM concentration in a PFA-100 assay. Error bars represent the mean±SEM. Each data point was performed in duplicate.

FIG. 14A: VWF Aptamer Ch-9.14-T10-treated animals maintained carotid artery patency following ferric chloride induced damage of murine carotid arteries. Transit time or blood flow (ml/min) through the damaged carotid artery did not decline in animals treated with the aptamer compared to control animals treated with PBS whose carotid blood flow ceased during the course of the experiment (n=11 per group). Squares (■) represent aptamer Ch-9.14-T10-treated animals. Open circles (○) represent phosphate-buffered saline (PBS)-treated animals. No significant change was observed in the blood flow in the aptamer-treated group during the course of the experiment. However, a significant difference in blood flow between the aptamer Ch-9.14-T10-treated mice and mice that did not receive the aptamer was observed (p<0.0001). X-axis represents time in minutes (min) over which the experiment took place. Y-axis represents transit time or blood flow in milliliters per minute (ml/min). A transit time of 0 indicates that the carotid artery is completely occluded. Error bars represent mean±SEM. FIGS. 14B and 14C: Carotid arteries of Aptamer Ch-9,14-T10-treated (FIG. 14B) animals maintained 100% patency while all animals that did not receive the aptamer (FIG. 14C) had thrombi that completely occluded their damaged carotid arteries (p<0.0001) (n=11 per group). Histopathological sections were stained with hematoxylin and eosin.

FIG. 16A: Antidote oligonucleotide (SEQ ID NOs:68-74, respectively, in order of appearance) design based upon Watson-Crick base-pairing to aptamer VWF Ch-9.14-T10 (SEQ ID NO:67) (top). FIG. 16B: Antidote oligonucleotide 1 (AO1) completely reverses the activity of Aptamer Ch-9.14-T10 (50 nM) as measured in the PFA-100 assay. Each antidote oligonucleotide (AO) was added in 50-fold molar excess over aptamer Ch-9.14-T10. Y-axis represent closing time in seconds (s). Error bars represent mean and SEM. All measurements were done in duplicate. FIG. 16C: AO1 and FIG. 16D: the Universal antidote CDP reverse that activity of Aptamer Ch-9.14-T10 in a PFA-100 assay at 10-fold molar excess over aptamer. AO1 and CDP were added in a 5 to 20-fold molar excess of 50 nM aptamer Ch-9.14-T10. Negative control samples that did not receive an antidote were treated with phosphate-buffered saline. Y-axis represent closing time in seconds (s). Error bars represent mean and SEM. All measurements were done in duplicate.

FIG. 17A: AO1 or CDP can reverse the activity of aptamer Ch-9.14-T10 in surgically challenged animals. Mice (n=5 per group) were treated with aptamer Ch-9.14-T10 (3 mg/kg) by intraperitoneal injection. AO1 or CDP were administered at a10-fold molar excess over aptamer via tail vein injection, then the animals were surgically challenged by clipping their tails and blood loss was measured. Animals that did not receive an antidote experienced significant blood loss compared to those given either or the antidotes (AO1- and CDP compared to no antidote, p<0.0001). However, no significant difference was observed in blood loss from animals given the aptamer and either of the antidotes (AO1-treated or CDP-treated) and animals not given the aptamer (p=0.74). FIG. 17B: CDP reverses the activity of the anti-FIXa aptamer Ch9.3T aptamer and the VWF aptamer Ch-9.14-T10 simultaneously. Mice (n=5 per group) were treated with the VWF aptamer (3 mg/kg) alone, the anti-FIXa aptamer (10 mg/kg) alone or both aptamers. Animals were then given antidote oligonucleotides A01 (for VWF aptamer) or 5-2C (for FIXa aptamer), the universal antidote CDP or no antidote (PBS vehicle control) and surgically challenged. Administration of antidote oligonucleotides A01 and 5-2C to animals that received both aptamers decreased blood loss significantly compared to the negative control antidote (p=0.03) but this was well above blood loss levels from animals that did not receive either aptamer. Blood loss from animals that received both aptamers and the universal antidote (CDP) was similar to that from mice that did not receive either aptamer (untreated, p=0.27) (Y-axis shows blood loss in microliters (µl)). Error bars represent the mean±SEM.

DETAILED DESCRIPTION OF THE INVENTION

Figure 1:
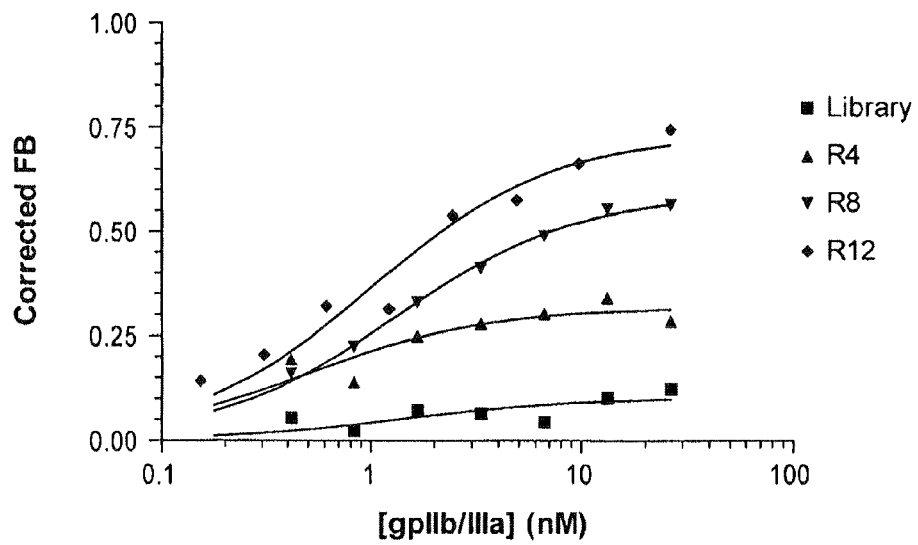
FIG. 1: Affinity of rounds to platelets. While the progress of the selection to gpIIb/IIIa was monitored by real-time PCR, the binding was measured on whole platelets using 32P RNA and nitrocellulose partitioning scheme. The [gpIIb/IIIa] was determined by assuming 80,000 gpIIb/IIIa molecules per platelet (Tcheng, Am. Heart J. 139:S38-45 (2000)). ■=Sel2 library; ▲=round 4; ▼=round 8; ♦=round 12.

The present invention relates generally to aptamers (DNA or RNA) that can bind to receptors and inhibit cell-cell or cell-particle interactions. The present invention relates, more specifically, to antiplatelet compounds (e.g., aptamers (DNA or RNA) and to methods of using same in the treatment of, for example, cardiovascular disease. In a preferred embodiment, the invention relates to RNA ligands or aptamers that can: i) bind to and inhibit the activity of gpIIb/IIIa, an integrin on the surface of platelets that is principally responsible for platelet aggregation, or ii) bind to VWF, a multimeric blood glycoprotein involved in coagulation, and inhibit platelet adhesion and aggregation. The invention also relates to antidote molecules that can bind to and reverse aptamer-induced platelet inhibition. The antiplatelet agent/antidote pairs of the present invention provide physicians with enhanced control over antithrombotic therapy.

Aptamers suitable for use as antiplatelet compounds (e.g., via their ability to bind to and inhibit the activity of gpIIb/IIIa or their ability to bind to VWF) and be prepared using SELEX methodology (see, for example, U.S. Pat. Nos. 5,270,163, 5,817,785, 5,595,887, 5,496,938, 5,475,096, 5,861,254, 5,958,691, 5,962,219, 6,013,443, 6,030,776, 6,083,696, 6,110,900, 6,127,119, 6,147,204, U.S. Appln 20030175703 and 20030083294, Potti et al, Expert Opin. Biol. Ther. 4:1641-1647 (2004), Nimjee et al, Annu. Rev. Med. 56:555-83 (2005)). The SELEX process consists of iterative rounds of affinity purification and amplification of oligonucleotides from combinatorial libraries to yield high affinity and high specificity ligands. Combinatorial libraries employed in SELEX can be front-loaded with 2' modified RNA nucleotides (e.g., 2' fluoro-pyrimidines) such that the aptamers generated are highly resistant to nuclease-mediated degradation and amenable to immediate activity screening in cell culture or bodily fluids.

Specific aptamers suitable for use as antiplatelets are described in the Examples that follow.

Aptamers of the invention can be used in the treatment of a cardiovascular disease in humans and non-human animals. For example, these aptamers can be used in patients undergoing PCI and can be used in the treatment of ACS (including stroke and arterial thrombosis). Use of the instant aptamers is expected to significantly reduce the morbidity and mortality associated with thrombosis.

The present invention also relates to antidotes for the antiplatelet aptamers described herein. These antidotes can comprise oligonucleotides that are reverse complements of segments of the antiplatelet aptamers. In accordance with the invention, the antidote is contacted with the targeted aptamer under conditions such that it binds to the aptamer and modifies the interaction between the aptamer and its target molecule (e.g., gpIIb/IIIa or VWF). Modification of that interaction can result from modification of the aptamer structure as a result of binding by the antidote. The antidote can bind free aptamer and/or aptamer bound to its target molecule.

Antidotes of the invention can be designed so as to bind any particular aptamer with a high degree of specificity and a desired degree of affinity. The antidote can be designed so that upon binding to the targeted aptamer, the three-dimensional structure of that aptamer is altered such that the aptamer can no longer bind to its target molecule or binds to its target molecule with less affinity.

Antidotes of the invention include any pharmaceutically acceptable agent that can bind an aptamer and modify the interaction between that aptamer and its target molecule (e.g., by modifying the structure of the aptamer) in a desired manner. Examples of such antidotes include oligonucleotides complementary to at least a portion of the aptamer sequence (including ribozymes or DNAzymes or peptide nucleic acids (PNAs)), nucleic acid binding peptides, polypeptides or proteins (including nucleic acid binding tripeptides (see, generally, Hwang et al, Proc. Natl. Acad. Sci. USA 96:12997 (1999)), and oligosaccharides (e.g., aminoglycosides (see, generally, Davies et al, Chapter 8, p. 185, RNA World, Cold Spring Harbor Laboratory Press, eds Gestlaad and Atkins (1993), Werstuck et al, Science 282:296 (1998), U.S. Pat. Nos. 5,935,776 and 5,534,408). (See also Chase et al, Ann. Rev. Biochem. 56:103 (1986), Eichhorn et al, J. Am. Chem.

Soc. 90:7323 (1968), Dale et al, Biochemistry 14:2447 (1975) and Lippard et al, Acc. Chem. Res. 11:211 (1978)).

Standard binding assays can be used to screen for antidotes of the invention (e.g., using BIACORE assays). That is, candidate antidotes can be contacted with the aptamer to be targeted under conditions favoring binding and a determination made as to whether the candidate antidote in fact binds the aptamer. Candidate antidotes that are found to bind the aptamer can then be analyzed in an appropriate bioassay (which will vary depending on the aptamer and its target molecule) to determine if the candidate antidote can affect the binding of the aptamer to its target molecule.

In a preferred embodiment, the antidote of the invention is an oligonucleotide that comprises a sequence complementary to at least a portion of the targeted aptamer sequence. Advantageously, the antidote oligonucleotide comprises a sequence complementary to 6-25 consecutive nucleotides of the targeted aptamer, preferably, 8-20 consecutive nucleotides, more preferably, 10-15 consecutive nucleotides.

Formation of duplexes by binding of complementary pairs of short oligonucleotides is a fairly rapid reaction with second order association rate constants generally between $1 \times 10^6$ and $3 \times 10^6 \, M^{-1} \, s^{-1}$. Thus, the effect on an aptamer by formation of a duplex with a complimentary oligonucleotide is rapid. Stability of short duplexes is highly dependent on the length and base-composition of the duplex. The thermodynamic parameters for formation of short nucleic acid duplexes have been rigorously measured, resulting in nearest-neighbor rules for all possible base pairs such that accurate predictions of the free energy, $T_m$ and thus half-life of a given oligoribonucleotide duplex can be calculated (e.g., Xia et al, Biochem. 37:14719 (1998) (see also Eguchi et al, Antisense. RNA, Annu. Rev. Biochem. 60:631 (1991)).

Antidote oligonucleotides of the invention can comprise modified nucleotides that confer improved characteristics, such as improved in vivo stability and/or improved delivery characteristics. Examples of such modifications include chemical substitutions at the sugar and/or backbone and/or base positions. Oligonucleotide antidotes can contain nucleotide derivatives modified at the 5- and 2' positions of pyrimidines, for example, nucleotides can be modified with 2' amino, 2'-fluoro and/or 2'-O-methyl. Modifications of the antidote oligonucleotides of the invention can include those that provide other chemical groups that incorporate additional charge, polarization, hydrophobicity, hydrogen bonding and/or electrostatic interaction. Such modifications include but are not limited to, 2' position sugar modifications, locked nucleic acids, 5 position pyrimidine modifications, 8 position purine modifications, modification at exocyclic amines, substitution of 4-thiouridine, substitution of 5-bromo or 5-iodo-uracil, backbone modifications, phosphorothioate or alkyl phosphate modifications, methylations, unusual base-pairing combinations such as isobases isocytidine and isoguanidine, etc. Modifications can also include 3' and 5' modifications, such as capping, and addition of PEG or cholesterol. (See also Manoharan, Biochem. Biophys. Acta 1489: 117 (1999); Herdewijn, Antisense Nucleic Acid Drug Development 10:297 (2000); Maier et al, Organic Letters 2:1819 (2000)).

A typical aptamer possesses some amount of secondary structure—its active tertiary structure is dependent on formation of the appropriate stable secondary structure. Therefore, while the mechanism of formation of a duplex between a complementary oligonucleotide antidote of the invention and an aptamer is the same as between two short linear oligoribonucleotides, both the rules for designing such interactions and the kinetics of formation of such a product are impacted by the intramolecular aptamer structure. The rate of nucleation is important for formation of the final stable duplex, and the rate of this step is greatly enhanced by targeting the oligonucleotide antidote to single-stranded loops and/or single-stranded 3' or 5' tails present in the aptamer. For the formation of the intermolecular duplex to occur, the free energy of formation of the intermolecular duplex has to be favorable with respect to formation of the existing intramolecular duplexes within the targeted aptamer. Thus, oligonucleotide antidotes of the invention are advantageously targeted at single-stranded regions of the aptamer. This facilitates nucleation and, therefore, the rate of aptamer activity modulation, and also, generally leads to intermolecular duplexes that contain more base pairs than the targeted aptamer.

Various strategies can be used to determine the optimal site for oligonucleotide binding to a targeted aptamer. An empirical strategy can be used in which complimentary oligonucleotides are "walked" around the aptamer. In accordance with this approach, 2'Omethyl oligonucleotides (e.g., 2'Omethyl oligonucleotides) about 15 nucleotides in length can be used that are staggered by about 5 nucleotides on the aptamer (e.g., oligonucleotides complementary to nucleotides 1-15, 6-20, 11-25 etc. of aptamer 9.3t). An empirical strategy may be particularly effective because the impact of the tertiary structure of the aptamer on the efficiency of hybridization can be difficult to predict. Assays described, for example, iii U.S. Appln. No. 20030083294 can be used to assess the ability of the different oligonucleotides to hybridize to a specific aptamer, with particular emphasis on the molar excess of the oligonucleotide required to achieve complete binding of the aptamer. The ability of the different oligonucleotide antidotes to increase the rate of dissociation of the aptamer from its target molecule can also be determined by conducting standard kinetic studies using, for example, BIACORE assays. Oligonucleotide antidotes can be selected such that a 5-50 fold molar excess of oligonucleotide, or less, is required to modify the interaction between the aptamer and its target molecule in the desired manner.

Alternatively, the targeted aptamer can be modified so as to include a single-stranded tail (3' or 5') in order to promote association with an oligonucleotide modulator. Suitable tails can comprise 1 to 20 nucleotides, preferably, 1-10 nucleotides, more preferably, 1-5 nucleotides and, most preferably, 3-5 nucleotides (e.g., modified nucleotides such as 2'Omethyl sequences). Tailed aptamers can be tested in binding and bioassays (e.g., as described in U.S. Appln. No. 20030083294) to verify that addition of the single-stranded tail does not disrupt the active structure of the aptamer. A series of oligonucleotides (for example, 2'Omethyl oligonucleotides) that can form, for example, 1, 3 or 5 basepairs with the tail sequence can be designed and tested for their ability to associate with the tailed aptamer alone, as well as their ability to increase the rate of dissociation of the aptamer from its target molecule.

The present invention relates to antidotes that specifically and rapidly reverse the anticoagulant and antithrombotic effects of aptamers that target gpIIb/IIIa and VWF. In accordance with this embodiment, antidotes (advantageously, oligonucleotide inhibitors) are administered that reverse the aptamer activity.

At least three clinical scenarios exist in which the ability to rapidly reverse the activity of an antithrombotic, anticoagulant or antiplatelet aptamer is desirable. The first case is when anticoagulant or antithrombotic treatment leads to hemorrhage. The potential for morbidity or mortality from this type of bleeding event can be a significant risk. The second case is when emergency surgery is required for patients who have received antithrombotic treatment. This clinical situation can arise, for example, in patients who require emergency coronary artery bypass grafts while undergoing PCI under the coverage of gpIIb/IIIa inhibitors. The third case is when an anticoagulant aptamer is used during a cardiopulmonary bypass procedure. Bypass patients are predisposed to post operative bleeding. In each case, acute reversal of the anticoagulant effects of an aptamer via an antidote (e.g., an oligonucleotide antidote targeted to an anticoagulant or antithrombotic aptamer) allows for improved, and likely safer, medical control of the anticoagulant or antithrombotic compound.

The aptamers and antidotes of the invention can be formulated into pharmaceutical compositions that can include, in addition to the aptamer or antidote, a pharmaceutically acceptable carrier, diluent or excipient. The precise nature of the composition will depend, at least in part, on the nature of the aptamer or antidote and the route of administration. Optimum dosing regimens can be readily established by one skilled in the art and can vary with the aptamer and antidote, the patient and the effect sought. Because the antidote activity is durable, once the desired level of modulation of the aptamer by the antidote is achieved, infusion of the antidote can be terminated, allowing residual antidote to clear the human or non-human animal. This allows for subsequent re-treatment of the human or animal with the aptamer as needed. Alternatively, and in view of the specificity of antidote oligonucleotides of the invention, subsequent treatment can involve the use of a second, different aptamer/antidote oligonucleotide pair.

The aptamers and antidotes can be administered directly (e.g., alone or in a liposomal formulation or complexed to a carrier (e.g., PEG)) (see for example, U.S. Pat. No. 6,147,204 for examples of lipophilic compounds and non-immunogenic high molecular weight compounds suitable for formulation use). Alternatively, oligonucleotide antidotes of the invention can be produced in vivo following administration of a construct comprising a sequence encoding the oligonucleotide. Techniques available for effecting intracellular delivery of RNA antidotes of gene expression can be used (see generally Sullenger et al, Mol. Cell. Biol. 10:6512 (1990)). (Also incorporated by reference is the following citation that describes APTT and other clotting assays: Quinn et al, J. Clin. Lab. Sci. 13(4):229-238 (2000). This review describes the properties and biochemistry of various clotting assays including APTT, PT and thrombin time assays, and their use in diagnosing coagulopathies.)

In addition to antidote oligonucleotides described above, and methods of using same, the invention also relates to the use of antidotes that bind in a sequence independent manner described, for example, in U.S. Provisional Application No. 60/920,807 and to method of using same to modulate (e.g., reverse or inhibit) the activity of aptamers described herein (see also application Ser. No. 12/588,016).

Certain aspects of the invention can be described in greater detail in the non-limiting Examples that follows. (See also Oney et al, Oligonucleotides 17:265-274 (2007)).

EXAMPLE 1

Experimental Details
Binding gpIIb/IIIa to plates

An enzyme linked immunosorbant assay (ELISA) was used to assess gpIIb/IIIa adherence to Immulon 4HBX plates. Briefly, 100 pmol gpIIb/IIIa was incubated with the Immulon 4HBX plates at 4° C. overnight. After washing 5× with TMB buffer (20 mM Hepes, pH: 7.4; 120 mM NaCl; 5 nM KCl; 1 mM $CaCl_2$; 1 mM $MgCl_2$; 0.01% BSA), wells were blocked with 1% BSA at room temperature for 1 h. The wells were washed 5× and incubated at 37° C. for 2 hrs with 10 µg/mL CD41, a mouse anti-human antibody that recognizes the gpIIb/IIIa complex), CD61 (a mouse anti-human antibody that recognizes the $\beta_3$-subunit of the protein (Southern Biotechnology Associates, Birmingham, Ala.)) or buffer. After washing 5×, 1:80,000 (v/v) goat anti-mouse IgG-HRP (Jackson ImmunoResearch Laboratories, Inc., West Grove, Pa.) was added and incubated at room temperature for 2 h. The wells were washed 5× and TMB substrate (Sigma-Aldrich, St. Louis, Mo.) was added. The plate was covered with aluminum foil and placed on a shaker for 15 min. In order to quench the reaction, 0.1 M sulfuric acid was added and the plate was scanned at 450 nm using an EL311 Microplate Autoreader (Bio-tek Instruments, Inc., Winooski, Vt.).

Selection of RNA Ligands to gpIIb/IIIa

Using the data from the gpIIb/IIIa bound to platelets, 100 µmol of gpIIb/IIIa (Enzyme Research, South Bend, Ind.) in HEPES-buffered saline and 1 mM $CaCl_2$ was bound to Immulon 4HBX plates (Thermo Electron Corporation, Boston, Mass.) at 4° C. overnight. The plates were then washed 3× with binding buffer (20 mM HEPES, pH: 7.4; 120 mM NaCl; 5 nM KCl; 1 mM $CaCl_2$; 1 mM $MgCl_2$; 0.01% BSA) and blocked with 3% BSA at room temperature for 1 h. In order to pre-clear plate-binding aptamers, no-protein wells (i.e., wells that had no gpIIb/IIIa in them) were also blocked with BSA and, after washing, RNA was added to nude wells and incubated at 37° C. for 1 h. The protein-blocked wells were washed 3× with binding buffer and the RNA from the nude wells was transferred to the protein-coated wells and incubated at 37° C. for 2 h. The wells were washed 3× and 75 µL of elution buffer (10 mM HEPES pH: 7.4; 120 mM NaCl; 5 mM KCl; 5 mM EDTA pH: 8.0) was added to wells and incubated at 37° C. for 30 min before being transferred to tubes. The eluted RNA ligands were reverse-transcribed and amplified as described (Drolet et al, Combinatorial Chemistry & High Throughput Screening 2:271-278 (1999)).

Binding Assays

Aptamer binding to purified platelets. Platelets were purified from freshly drawn blood from healthy volunteers (Hoffman et al, Am. J. Clin. Pathol. 98:531-533 (1992)). Briefly, platelets were isolated by density gradient centrifugation, then separated from plasma proteins by gel-filtration over 50 mL column of Sepharose Cl-2B in Tyrodes buffer (15 mM HEPES, pH 7.4; 3.3 mM $Na_2PO_4$; 138 mM NaCl, 2.7 mM KCl; 1 mM $MgCl_2$, 5.5 mM dextrose) with 1 mg/mL bovine serum albumin. The platelets were activated prior to binding with 1 nM thrombin; 1 mM $CaCl_2$ and 200 ng/mL convulxin.

Dissociation constants ($K_d$) were determined using a double-filter, nitrocellulose binding method (Wong et al, Proc. Natl. Acad. Sci. USA 90:5428-5432 (1993)). Briefly, RNA was dephosphorylated using bacterial alkaline phosphatase (Gibco BRL, Gaithersberg, Md.) and end-labeled at the 5' with T4 polynucleotide kinase (New England Biolabs, Beverly, Mass.) and [$\gamma^{32}$P]ATP (Amersham Pharmacia Biotech, Piscataway, N.J.) (Fitzwater et al, Methods Enzymol. 267:275-301 (1996)). Direct binding was performed by incubating $^{32}$P-RNA with purified platelets in platelet counts ranging 100,000 to 97/µL in Tyrodes buffer+1 mg/ml BSA at 37° C. The fraction bound of the nucleic acid-protein complex was quantified with a Phosphoimager (Molecular Dynamics, Sunnyvale, Calif.). The non-specific binding of radiolabeled nucleic acid was subtracted (Wong et al, Proc. Natl. Acad. Sci. USA 90:5428-5432 (1993)).

RNA binding to gpIIb/IIIa. To measure aptamer binding to gpIIb/IIIa, RNA was 5'-biotinylated and assayed in an enzyme linked oligonucleotide assay (ELONA) (Drolet et al, Nat. Biotechnol. 14:1021-1025 (1996)). Briefly, biotin was appended to the 5' end of the RNA by standard transcription protocols using 4-fold molar excess of 5'-biotin GMP over GTP in the reaction mixture. Immulon 2 wells were coated overnight at 4° C. with gpIIb/IIIa. The wells were washed and blocked with 3% bovine serum albumin (BSA) for 1 h at room temperature. Two-fold serial dilutions of RNA from 1 µM to 980 pM were performed and the RNA was incubated in the protein-coated well at 37° C. for 45 min. Unbound RNA was removed by washing. To detect bound RNA, 1:1000 streptavidin-alkaline phosphate conjugate (Sigma-Aldrich Corp., St. Louis, Mo.) was incubated in the wells for 30 min at room temp. Finally p-nitrophenyl phosphate (Sigma-Aldrich Corp., St. Louis, Mo.) was used as a substrate and, after addition, absorbance at 405 nm was measured every 30 sec over 30 min in a EL311 Microplate Autoreader (Bio-tek Instruments, Inc., Winooski, Vt.). Binding data is fit to an equation that describes the fraction of RNA bound as a function of $K_d$ for monophasic binding behavior.

Competition Assay

The assay was carried out as above with the exception that after addition of 5'-biotinylated RNA, either a) buffer, b) cold (unlabeled with $^{32}P$) gpIIb/IIIa RNA, c) Abciximab (Eli Lilly, Indianapolis, Ind.) or d) Eptifibatide (COR Therapeutics Inc, San Fran Francisco, Calif.) was added at two-fold serial dilutions between 100 to 0.1-fold excess of the compound's dissociation constant.

Functional Assays

Platelet Function Analysis (PFA). Platelet Function Analyzer, PFA-100 (Dade Behring, Deerfield, Ill.) provides a quantitative measure of platelet function in anti-coagulated whole blood (Ortel et al, Thromb. Haemost. 84:93-97 (2000)). Briefly, 800 µL of whole blood was mixed with aptamers in a platelet binding buffer consisting of 150 mM NaCl; 20 mM HEPES pH: 7.4; 5 mM KCl; 1 mM $MgCl_2$ and $CaCl_2$. The maximum closing time of the PFA-100 is 300 seconds. Antidote activity of aptamer was measured by mixing whole blood with aptamer in buffer followed by administration of antidote and measuring in PFA.

Platelet Aggregometry. Chrono-log Whole Blood Lumi Ionized Aggregometer (Chrono-log, Haverton, Pa.) provided a measurement of platelet aggregation in platelet-rich plasma. Briefly, platelet-rich plasma (PRP) was isolated from whole blood and 450 µl of PRP, 50 µl of aptamer and 50 µl Chonolume were added. After calibrating the instrument, 5 µl of ADP agonist was added and transmission was measured for 6 minutes.

Results

A solid phase platform of SELEX was utilized whereby the protein was adsorbed to plates and the presence and integrity of the protein was verified by ELISA. In this assay, two antibodies were used, CD41, which recognized the gpIIb/IIIa complex, and CD61, which recognizes the $β_3$ subunit of the heterodimer. Ethylene diamine tetra-acetic acid (EDTA), a calcium chelator, was used to demonstrate the confirmation-specific nature of gpIIb/IIIa. It was clear that both human and porcine gpIIb/IIIa on the plates were in a confirmation that was recognized by both antibodies without EDTA.

After determining that the protein was adsorbed to the plates and was recognized by both complex- and monomer-specific antibodies, a 'toggle' selection was performed in order to isolate RNA ligands that bound to both human and porcine orthologs (Ginsberg et al, Hematology (1):339-357 (2001)). The selection was monitored using real-time PCR as described (Lupoid et al, Cancer Research 62:4029-4033 (2002)). As illustrated in Table 1, the signal from the enrichment from the gpIIb/IIIa wells was above that of the no protein well. At round 12, there was a 113-fold increase in the signal to background and this was interpreted to represent a significant enrichment of the RNA pool to gpIIb/IIIa. Subsequent rounds of selection resulted in a significantly reduced signal to background (data not shown), and at this point, round 12 was cloned and sequenced.

TABLE 1

| | Absolute RNA | | |
|---|---|---|---|
| Round | Protein | No protein | Signal/Background |
| 1 | — | — | — |
| 2 | — | — | — |
| 3 | 2.45E+00 | 2.50E+01 | 0.1 |
| 4 | 2.12E+01 | 7.93E+00 | 3 |
| 5 | 1.70E+02 | 1.05E+02 | 2 |
| 6 | 7.98E+01 | 1.59E+01 | 5 |
| 7 | 1.29E+02 | 9.41E+01 | 1 |
| 8 | 9.95E+01 | 1.48E+01 | 7 |
| 9 | 5.44E+00 | 2.31E+00 | 2 |
| 10 | 5.63E+01 | 3.51E+00 | 16 |
| 11 | 1.56E+02 | 2.32E+01 | 7 |
| 12 | 3.72E+01 | 3.28E−01 | 113 |

In order to correlate the real-time data with binding affinity, purified 11D platelets were isolated and the affinity of each round to activated platelets was measured using nitrocellulose-filter partitioning (Wang et al, Biochemistry 32:1899-1904 (1993)). Since purified gpIIb/IIIa were selected, 80,000 gpIIb/IIIa receptors per platelet were assumed (Tcheng, Am. Heart J. 139:S38-45 (2000)) and the theoretical concentration of the protein was calculated. While this certainly does not provide an accurate binding affinity, it was useful to validate the real-time PCR data. The binding data illustrated the increased affinity of the rounds to gpIIb/IIIa on platelets (FIG. 1). Moreover, the binding also correlated with signal:background data in Table 1, where round 12 bound to the platelets with the highest affinity (FIG. 1) and represented the highest signal:background in the selection.

Figure 2:
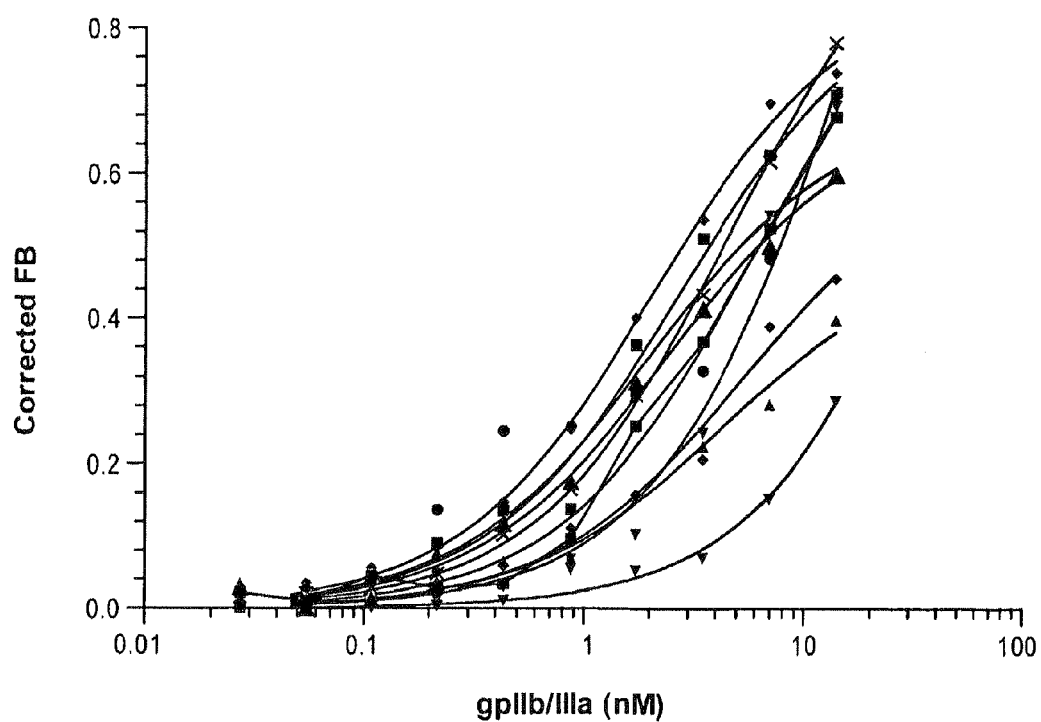
FIG. 2: Round 12 clones binding to platelets. Clones from round 12 bound to gpIIb/IIIa on platelets with different affinity. C1=■; C2=▲; C3=▼; C4=♦; C5=●; C6=■; C7=▲; C8=▼; C9=♦; C10=●.

The resulting clones from round 12 were clustered into 10 distinct families (Table 2). Representative clones from each family were subsequently tested for their ability to bind to purified platelets. Aptamer C5 had the highest affinity interaction with gpIIb/IIIa on platelets (apparent $K_d$=2 nM). Clone C1, which was the highest represented clone from round 12, had an apparent $K_d$=6 nM. Clone C3 was the poorest binder to gpIIb/IIIa, with an apparent $K_d$=62 nM (FIG. 2).

TABLE 2

| Clone | Sequence of N40 region | SEQ ID NO: | Frequency |
|---|---|---|---|
| C1 | TATAGACCACAGCCTGAGTATTAACCACCAACCCAGGTACT | 1 | 51% |
| C2 | TATAACCGTTCTAGCGCTAATGACACTATAGCATCCCCGT- | 2 | 2% |
| C3 | TGCCACATGCCTCAGATACAGCACGCACCTTCGACCTAAT- | 3 | 12% |

TABLE 2-continued

| Clone | Sequence of N40 region | SEQ ID NO: | Frequency |
|---|---|---|---|
| C4 | ACCTGCTAGCAGTGGCGCGAATAAACCATCGCAGCATCAA- | 4 | 2% |
| C5 | GGACTTGCGAGCCAGTCCACACGCCGC-GACTAAAGAGACTTCTC | 5 | 2% |
| C6 | ACAGATCTACCCGAGACAAACATCCCACCCTCCGA------ | 6 | 7% |
| C7 | TCCTAAGATTAAATACGCCACGGCTCACTTACACACCAG-- | 7 | 4% |
| C8 | TGCCACATGCCTCAGATACAGCACGCACCTTCGACCTAAT- | 8 | 12% |
| C9 | TCCCTTGGATGAGACTAACAACCTACCACATCCTA-TACTC | 9 | 4% |

Figure 3A:
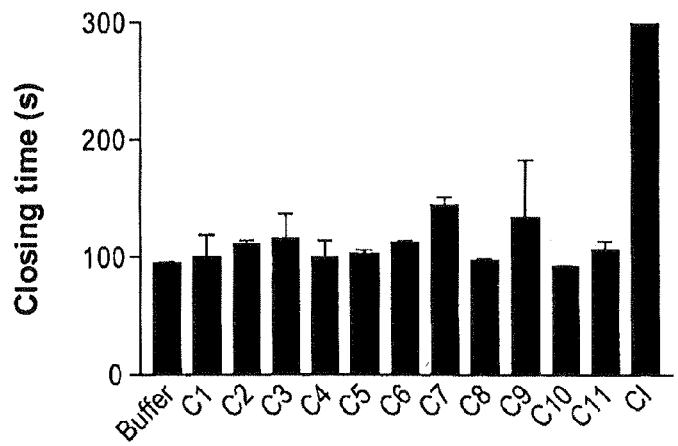
FIGS. 3A-3C: Functional activity of aptamers. Aptamers were tested in a PFA-100. All clones were tested in a volume of 840 μl at a final concentration of 1 μM (FIG. 3A). The ability of the aptamers to inhibit platelet function in pig blood was evaluated (FIG. 3B). Platelet activity of Cl was tested in a Chronolog Lumi-aggregometer (FIG. 3C). Error bars represent S.E.M.
Figure 3B:
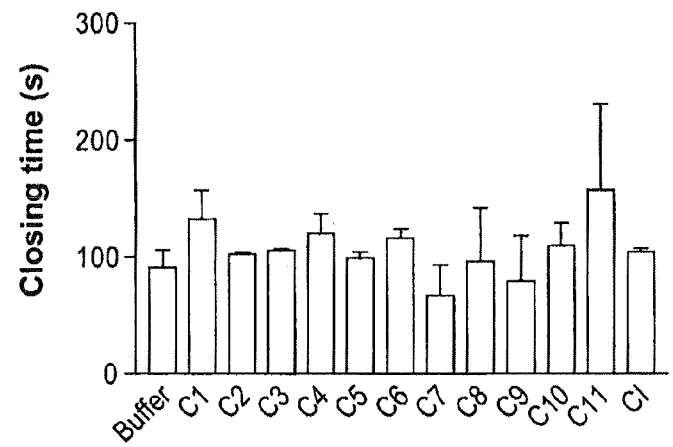

In order to assess the inhibitory activity of the aptamer on gpIIb/IIIa-mediated platelet aggregation, each aptamer was tested in a Platelet Function Analyzer (PFA-100). This device is sensitive to gpIIb/IIIa-mediated platelet inhibition with Abciximab and Eptifibatide (data not shown) (Hezard et al, Thromb. Haemost. 81:869-873 (1999)) and is an attractive assay as it measures platelet activity in whole blood under high shear conditions, which recapitulates the in vivo condition more reasonably than standard aggregometry (Harrison, Blood Rev. 19:111-123 (2005)). In addition to the clones isolated from the selection, an RNA aptamer generated to gpVb/IIIa, a related integrin to gpIIb/IIIa, designated Cl, was also tested. All the clones were tested in a volume of 840 µL at a final concentration of 1 µM (FIG. 3A). The baseline closing time of human whole blood was 95±1 s. Of the clones tested in human whole blood, Cl was the only aptamer that inhibited platelet aggregation to >300 s, exceeding the upper limit of the instrument. Given the binding data of the aptamers to platelets, the conclusion was that the aptamers isolated to gpIIb/IIIa bound to the ligand on platelets without affecting its function upon activation. An evaluation was then made of the ability of the aptamers to inhibit platelet function in pig blood to see if any of the isolated ligands had any effect. Not surprisingly, none of the aptamers tested had any effect in the PFA-100 and modestly deviated from the baseline closing time 91±15 s without significance (FIG. 3B).

Figure 3C:
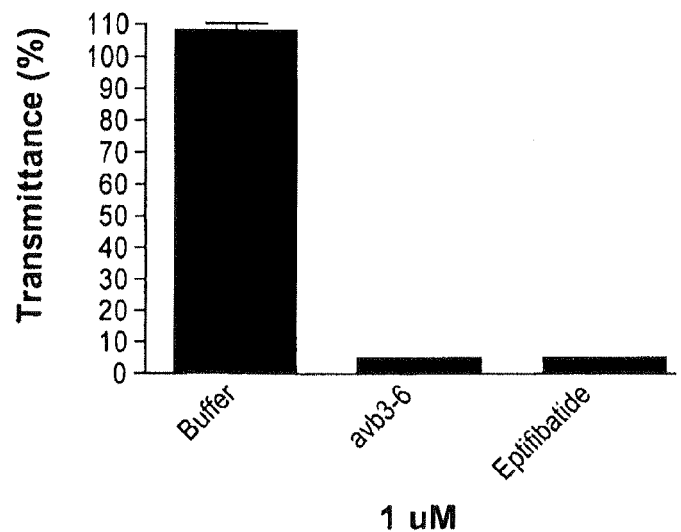

Finally, after determining the effect of Cl in PFA, a determination of the platelet activity was made in a more traditional assay. As shown in FIG. 3C, Cl was tested in a Chrono-log lumi-aggregometer. Transmittance of the negative control was 104±2%, while Cl was 5%. This was equivalent to Eptifibatide, which served as a positive control.

Figure 4:
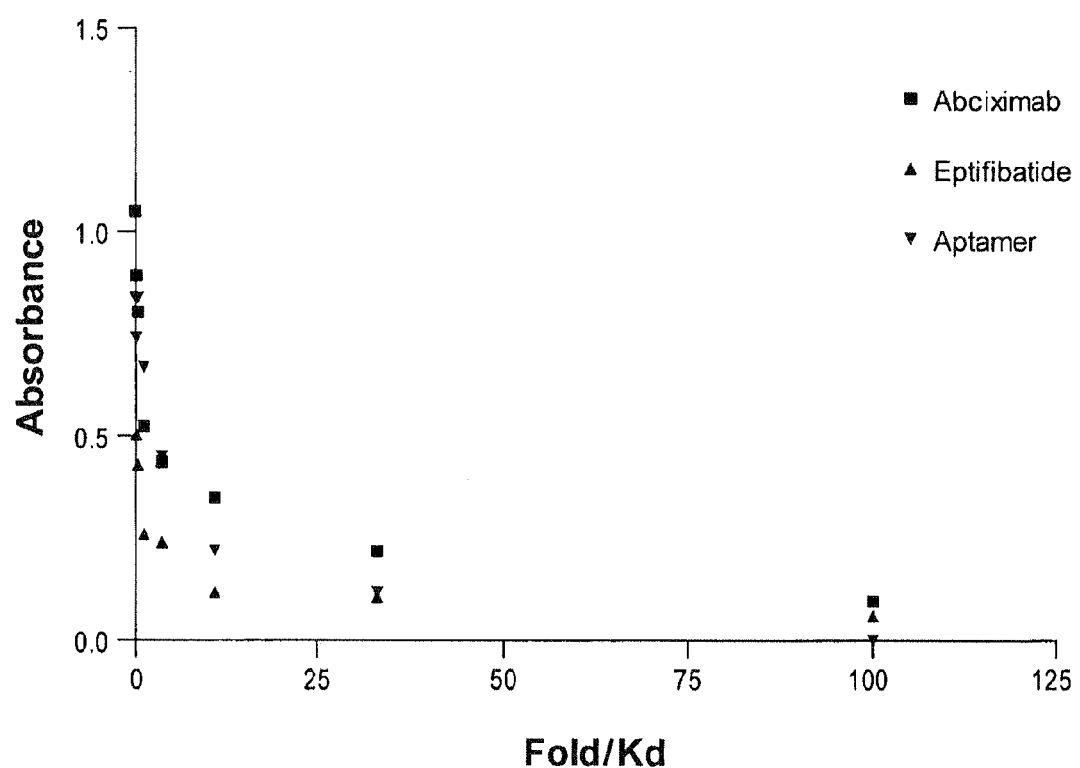
FIG. 4: Aptamer competes with current drugs for binding to gpIIb/IIIa. The assay was carried out in 3-fold serial dilutions between 100 to 0.1-fold excess of each compound's dissociation constant. ■=Abciximab; ▲=Eptifibatide; ▼=Aptamer.

In order to determine the binding affinity of Cl to gpIIb/IIIa, Cl was labeled with biotin at its 5'-end and bound to gpIIb/IIIa immobilized on plates (Drolet et al, Nat. Biotechnol. 14:1021-1025 (1996)), with a $K_d$ of 10±5 nM. To determine the binding region of Cl, the aptamer was then analyzed in a competition assay against Abciximab and Eptifibatide over a concentration range between 0.1- and 100-fold excess of the $K_d$ of each drug (FIG. 4). Both gpIIb/IIIa blockers competed with aptamer Cl in a concentration-dependent manner.

After establishing that Cl inhibited platelet aggregation in vitro, the activity of truncated versions of the molecule was assessed. It was determined that a modestly truncated version, designated Cl-6, was just as potent in inhibiting platelet aggregation, exceeding the closing time of 300 at a concentration of 500 nM. This level of inhibition was within the same range as Eptifibatide, which is extensively used in the clinic (Jackson et al, Nat. Rev. Drug Discov. 2:775-789 (2003)).

Figures 5A, 5B:
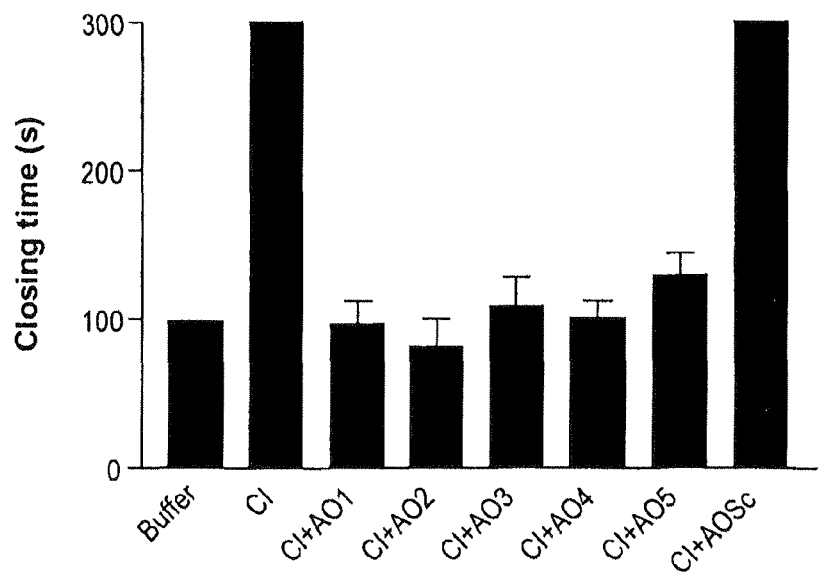
FIGS. 5A and 5B: Antidote reverses aptamer activity in PFA.

Once a concentration of Cl-6 that increased the closing time to >300 s had been identified, 5 antidote oligonucleotides (AO) were designed that were the reverse compliment of a segment of previous random region of Cl-6 (FIG. 5A). The AO were added at 10-fold molar excess of Cl-6 (AO 5 µM versus Cl-6 500 nM). Each antidote effectively reversed the activity of Cl-6 and their closing time was similar to baseline (P>0.05) (FIG. 5B). The most effective antidote, AO2, had a closing time of 81±19 s, while the least effective antidote, AO5, had a closing time of 130±15 s. A scrambled AO (AOSc) was used to verify that the reversal activity was specific to each antidote and not a consequence of the presence of additional nucleic acid in the assay. When mixed with Cl-6, AOSc resulted in a closing time of >300 s (FIG. 5B).

In summary, a solid-phase system of SELEX was employed to isolate 2'-fluoropyrimidine modified RNA aptamers that bound to gpIIb/IIIa with high affinity (FIG. 2). The aptamer with the highest affinity, C5, bound to gpIIb/IIIa on the surface of platelets with a $K_d$ of 2 nM. In evaluating gpIIb/IIIa-mediated platelet aggregation in whole blood, it was demonstrated that aptamer Cl exceeded the upper limit of the assay with a closing time>300 s in human blood. A truncated version of this aptamer, Cl-6, retained inhibitory activity in the PFA-100 assay. It was interesting that the other aptamers isolated to gpIIb/IIIa did not have inhibitory activity despite high affinity binding to the protein. It is possible the protein immobilized on the solid surface was in a conformation that prevented RNA ligand access to its functional epitope. Aptamer Cl did not have the highest affinity to gpIIb/IIIa yet was the only one with significant functional activity. Eptifibatide is illustrative of this, with a $K_d$ of 120 nM, compared to Abciximab, which has a $K_d$ of 5 nM (Scarborough et al, Circulation 100:437-444 (1999)).

After establishing the inhibitory effect of Cl, its binding was characterized. Not surprisingly, both Eptifibatide and Abciximab compete with the aptamer for binding to gpIIb/IIIa (FIG. 4). Abciximab is a humanized mouse Fab (also known as 7E3) that binds to both gpIIb/IIIa and gpVb/IIIa (Artoni et al, Proc. Natl. Acad. Sci. USA 101:13114-13120 (2004)). Binding analysis has shown that this antibody preferentially binds to active platelets over resting ones and its effect on gpIIb/IIIa inhibition is its interaction with the $\beta_3$ subunit (Artoni et al, Proc. Natl. Acad. Sci. USA 101:13114-13120 (2004)). Eptifibatide is cyclic heptapeptide modeled after a leucine-glycine-aspartic acid (KGD) sequence from pit viper venom (Coller, Thromb. Haemost. 86:427-443 (2001)). Its inhibitory action is on the arginine-glycine-aspardic acid (RGD) residue on gpIIb/IIIa (Scarborough et al, Circulation 100:437-444 (1999)). The RGD moiety binds to both gpIIb/IIIa and gpVb/IIIa as well and involves the $\beta_3$ subunit (Xiong et al, Science 296:151-155 (2002), Xiao et al, Nature 432:59-67 (2004)) and, therefore, either the aptamer is sterically hindering fibrinogen from accessing the RGD pocket between the $\alpha_2$ and $\beta_3$ pocket or preventing the receptor from forming the conformation necessary for fibrinogen binding.

All of the antidote oligonucleotides to Cl-6 functionally reversed the activity of the aptamer, returning the closing times to baseline levels (FIG. 5B). Rational design of AO is based on the assumption that the tertiary conformation of the aptamer can be disturbed by Watson-Crick base-pairing of AO to critical regions of the aptamer (Rusconi et al, Nat. Biotechnol. 22:1423-1428 (2004), Rusconi et al, Nature 419: 90-94 (2002)). There was insignificant variability between AOs as they all effectively inhibited the aptamer's anti-platelet activity. It was remarkable to see the rate of the aptamer-antidote binding. After incubation of the aptamer for 1 min, the antidote is added, carefully mixed and then tested. This fast aptamer-antidote interaction is very attractive as a regulatable therapeutic as it gives the clinician tight control of the anti-platelet agent and the ability to reverse its activity immediately in the event of a complication requiring normal platelet activity.

This anti-gpIIb/IIIa aptamer/antidote represents the first regulatable anti-platelet drug/antidote pair that has the potential to significantly improve morbidity in patients that require gpIIb/IIIa inhibitors.

EXAMPLE 2

Over the past decade, much research has elucidated the important role of platelets in cardiovascular disease. Excessive accumulation of platelets on atherosclerotic plaques is an essential aspect of thrombus formation, which, in turn, is responsible for the development of acute coronary syndromes like stroke and arterial thrombosis. A number of anti-platelet drugs exist that are routinely used in clinics. Aspirin inhibits thromboxane A2 and was the first anti-platelet agent used clinically. Clopidogrel and Ticlopidine inhibit ADP receptors PIIY1 and PIIY12 and Abciximab, Eptifibatide and Tirofiban are gpIIb/IIIa inhibitors, the most potent class of anti-platelet compounds to date. While these drugs have shown remarkable clinical efficiency in reducing the morbidity and mortality associated with thrombosis, these agents have a number of drawbacks, most significant of which is hemorrhage. Therefore, a pressing need exists for anti-platelet drugs with improved safety profiles that are targeted against a platelet receptor/ligand interaction involved in the common platelet activation pathway. Antidote development represents a key strategy to overcome the obstacle of hemorrhage and, in order to address this issue for anti-platelet therapies, von Willebrand Factor (VWF) inhibitors have been developed that have specific antidotes.

Using the SELEX technique, aptamers were isolated from a 2'-fluoropyrimidine-modified single-stranded RNA library containing a 40 nucleotide-randomized region that bind to VWF with high affinity and specificity. Employing the SELEX procedure yielded aptamers rapidly and made it possible to assess the inhibitory function in in vitro experiments. Previously, nuclease-resistant aptamers have been isolated that bind to and inhibit human factors Vila, IXa, Xa and IIa using "SELEX". As with numerous selection experiments previously conducted, nitrocellulose-filter binding was employed as the partitioning scheme. Briefly, $^{32}$P-end-labeled RNA aptamers (<0.1 nM) were incubated with the individual protein at a range of concentrations. The RNA-protein complexes were separated from the free RNA by passing the mixture through a nitrocellulose filter by vacuum. Bound and free RNA were quantified by phosphorimager analysis and the data fitted to yield the $K_d$s for the RNA aptamer-protein interaction. A decreasing $K_d$ value pointed to increasing affinity of RNA molecules for VWF. The RNA round that yielded a binding affinity in low nanomolar range is sequenced and individual clones are grouped into families based on their sequence similarity and structural conservation using computer-aided secondary structure analysis.

Figure 6:
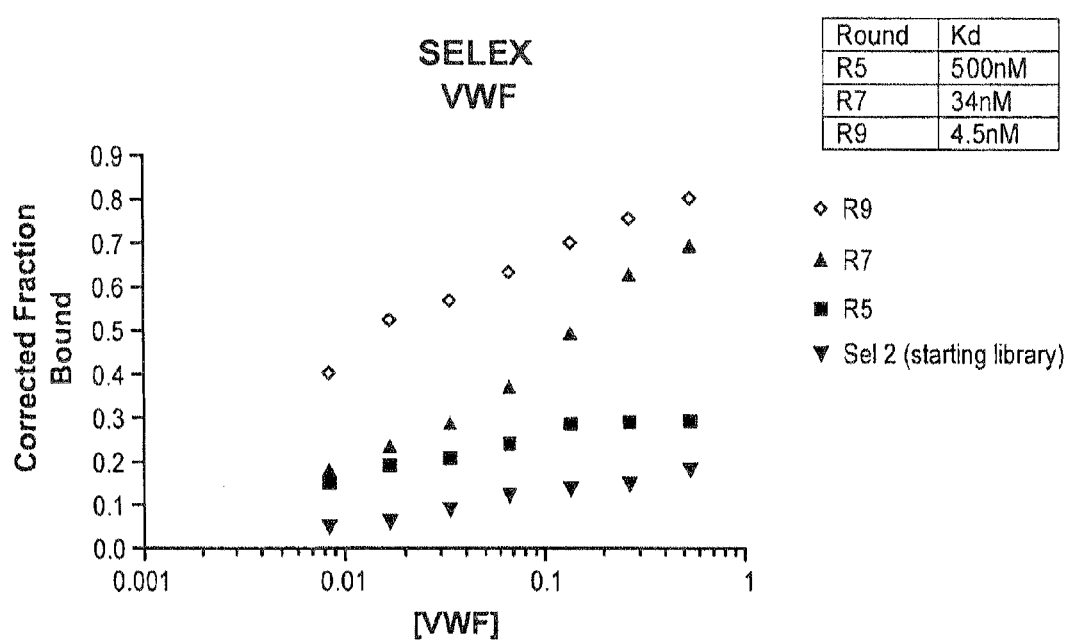
FIG. 6. Binding improved over consecutive rounds of VWF selection. Nitrocellulose filter binding assay with $^{32}$P labeled RNA molecules. Inverted triangles (▼) represent the original RNA library (Sel2). Squares (■) represent round 5, triangles (▲) represent round 7 and diamonds (◇) represent round 9 RNA pools. Y-axis is the fraction of RNA molecules bound at a given VWF protein concentration. Protein concentration given in micro molar (X-axis).
Figure 7:
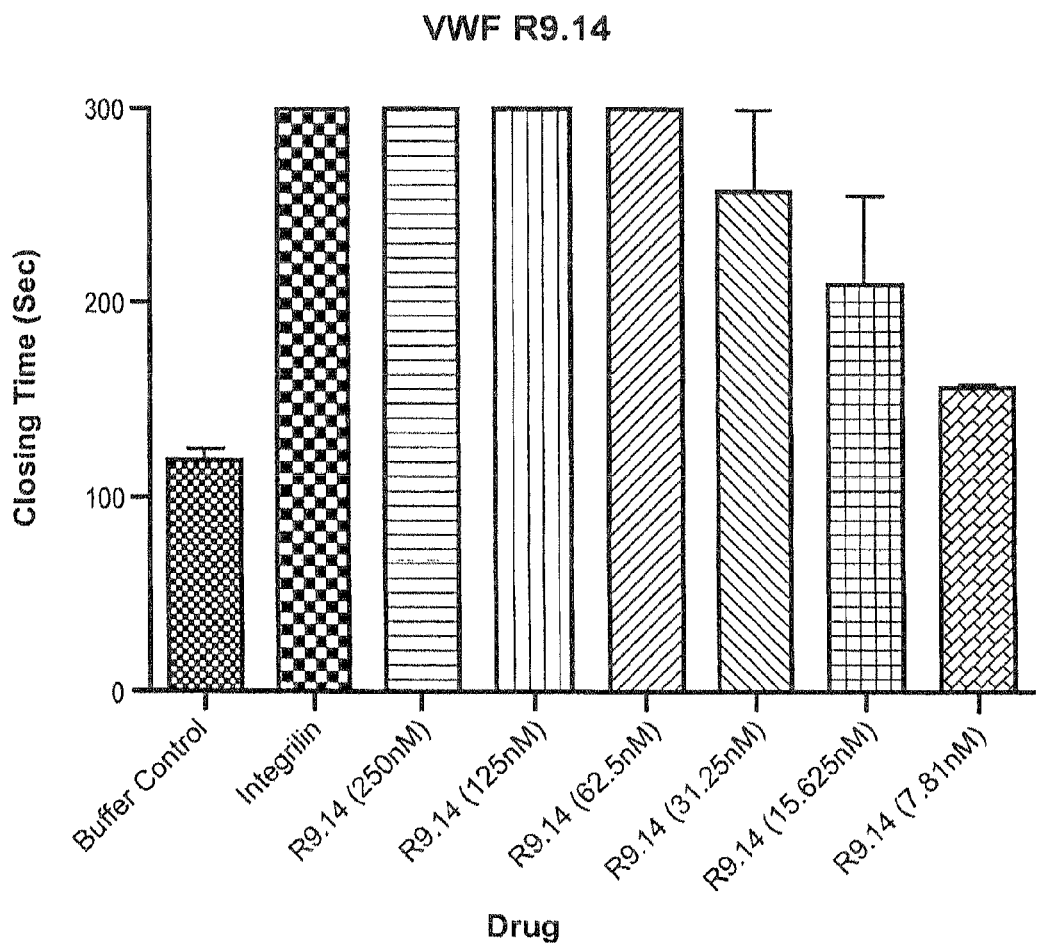
FIG. 7. Clone VWF R9.14 inhibits platelet activity in a PFA-100: VWF aptamer R9.14 was added to 800 microL whole blood at increasing is concentrations and a PFA-100 assay was performed to determine if the aptamer delayed platelet mediated closing. Integrilin is positive control. Each point has been performed in duplicate. Error bars represent the range of data.

VWF "SELEX": Using the starting library, 9 rounds of selection were performed to purified human VWF protein (obtained from Haemtech Inc.). There was a steady increase in binding affinity to VWF from the starting library to R9 (VWF selection round 9) (FIG. 6.). The Kd of round 9 reached the single digit nanomolar range, thus the individual clones making up the R9RNA pool were cloned and characterized. (See FIGS. 7 and 8.)

```
Clone VWF R9.14                          (SEQ ID NO: 10)
GGGAGGACGATGCGG-

TGGACGAACTGCCCTCAGCTACTTTCATGTTGCTGACGCA---

CAGACGACTCGCTGAGGATCC
```

Binding Affinities

Clone VWF R9.14 Kd=12 nM

```
SO VWF AO 1                              (SEQ ID NO: 11)
mC.mU.mU.mA.mA.mG.mC.mA.mG.mG.mA.mG.mA.mG.mC.mG.

mC.mG.mA.mU

SO VWF AO2                               (SEQ ID NO: 12)
mA.mG.mC.mU.mG.mC.mU.mU.mA.mA.mG.mC.mA.mG.mG.mA.

mG.mA.mG.mC

SO VWF AO3                               (SEQ ID NO: 13)
mU.mU.mG.mA.mU.mA.mG.mC.mU.mG.mC.mU.mU.mA.mA.mG.

mC.mA.mG.mG

SO VWF AO4                               (SEQ ID NO: 14)
mG.mC.mU.mA.mU.mU.mU.mG.mA.mU.mA.mG.mC.mU.mG.mC.

mU.mU.mA.mA

SO VWF AO5                               (SEQ ID NO: 15)
mA.mA.mG.mA.mU.mG.mG.mG.mC.mU.mA.mU.mU.mU.mG.mA.

mU.mA.mG.mC.mU.mG

Sel2 3' W1                               (SEQ ID NO: 16)
mT.mC.mT.mC.mG.mG.mA.mT.mC.mC.mT.mC.mA.mG.mC.mG.

mA.mG.mT.mC.mG.mT.mC.mT
```

EXAMPLE 3

To generate a safer, antidote-controllable VWF inhibitor, the decision was made to exploit the properties of nucleic acid ligands termed aptamers. As noted above, aptamers are single-stranded nucleic acid molecules that can directly inhibit protein function by binding to their targets with high affinity and specificity (Nimjee, Rusconi et al, Trends Cardiovasc. Med. 15:41-45 (2005)). To isolate RNA aptamers against VWF, a modified version of SELEX (Systematic Evolution of Ligands by EXponential enrichment), termed "convergent" SELEX, was performed. These aptamers bind to VWF with high affinity ($K_d$<20 nM) and inhibit platelet aggregation in Platelet Function Analyzer (PFA-100) and ristocetin induced platelet aggregation (RIPA) assays. Moreover, an antidote molecule that can quickly reverse such aptamers' function has been nationally designed. This antidote molecule can give physicians better control in clinics, enhancing the aptamers' safety profile.

Experimental Details

Generation of Aptamers

"Convergent" SELEX

The sequence of the starting RNA combinatorial library was 5'-GGGAGGACGATGCGG-$N_{40}$-CAGACGACTCGCTGAGGATCC-3' (SEQ ID NO: 17), where $N_{40}$ represents 40 completely random nucleotides. 2'F cytidine triphosphate and 2'F uridine triphosphate (Trilink Biotechnologies, San Diego, CA) were incorporated into the RNA libraries by in vitro transcription in order to confer nuclease resistance. The selection was carried out in selection buffer E (20 mM HEPES, pH 7.4, 50 mM NaCl, 2 mM $CaCl_2$, and 0.1% bovine serum albumin (BSA)) at 37° C. until round P5V2 and then continued in selection buffer F (20 mM HEPES, pH 7.4, 150 mM NaCl, 2 mM $CaCl_2$, and 0.1% bovine serum albumin (BSA)). RNA-VWF complexes were separated from unbound RNA by passing them over a nitrocellulose filter (BA 85, Whatman Inc, NJ).

Five rounds of SELEX were performed on the plasma proteome followed by four rounds of convergent SELEX as described by Layzer et al. (oligonucleotides 17:XX-XX (2007)). Briefly, the starting aptamer library (Sel2) was incubated with diluted normal human plasma at 37° C. for 15 minutes in selection buffer E. Yeast tRNA was used to inhibit non-specific binding of the aptamer library to the plasma proteome. Bound RNA aptamers were separated from unbound aptamers using a nitrocellulose filter. Following round 5 of plasma SELEX, convergent SELEX using VWF was performed for 4 rounds (2 rounds in selection buffer E followed by 2 rounds in selection buffer F).

Antidote Oligonucleotides

Antidote oligonucleotides were synthesized and purified by Dharmacon Research, Inc. 2'-O-methyl purines and pyrimidines were incorporated into the antidote oligonucleotides.

Binding Assays

Affinity constants ($K_d$ values) were determined using double-filter nitrocellulose filter binding assays (Rusconi et al, Thromb. Haemost. 84:841-848 (2000)). All binding studies were performed in either binding buffer E (20 mM HEPES, pH 7.4, 50 mM NaCl, 2 mM $CaCl_2$, and 0.1% BSA) or binding buffer F (20 mM HEPES, pH 7.4, 150 mM NaCl, 2 mM $CaCl_2$, and 0.1% BSA) at 37° C. Human purified VWF (factor VIII free) was purchased from Haematologic Technologies Inc. (Essex Junction, VT) and used in the double-filter nitrocellulose filter binding assay to determine the $K_d$ of every other round and individual clones. VWF SPI and VWF SPIII domains were kindly provided by Dr. J. Evan Sadler (Washington University in St. Louis). Briefly, RNA were dephosphorylated using bacterial alkaline phosphatase (Gibco BRL, Gaithberg, Md.) and end-labeled at the 5' end with T4 polynucleotide kinase (New England Biolabs, Beverly, Mass.) and [$\gamma^{32}$P] ATP (Amersham Pharmacia Biotech, Piscataway, N.J.) (Fitzwater and Polisky, Methods Enzymol. 267:275-301 (1996)). Direct binding was performed by incubating $^{32}$P-RNA with VWF in physiological buffer+1 mg/ml BSA at 37° C. for 5 min. The fraction of the nucleic acid-protein complex which bound to the nitrocellulose membrane was quantified with a posphoimager (Molecular Dynamics, Sunnyvale, Calif.). Non-specific binding of the radiolabeled nucleic acid was subtracted out of the binding such that only specific binding remained (Wong and Lohman, Proc. Natl. Acad. Sci. USA 90:5428-5432 (1993)).

Platelet Function Analysis

PFA-100

The Platelet Function Analyzer, PFA-100 (Dade Behring, Deerfield, Ill.), measures platelet function in terms of clot formation time. In this assay, collagen/ADP cartridges were utilized to activate the platelets and measure the amount of time taken to form a clot in anticoagulated whole blood (Harrison, Blood Rev. 19:111-123 (2005)). Briefly, 840 μL of whole blood was mixed with aptamer in platelet binding buffer (150 mM NaCl; 20 mM Hepes pH: 7.4; 5 mM KCl; 1 mM $MgCl_2$ and 1 mM $CaCl_2$) and incubated for 5 minutes at room temperature. This mixture was then added to a collagen/ADP cartridge and tested for its closing time. The maximum closing time of the PFA-100 is 300 seconds. Antidote activity of the aptamer was measured by mixing whole blood with aptamer, incubating for 5 minutes followed by addition of antidote or buffer, and testing the mixture in the PFA-100.

Platelet Aggregometry

A Chrono-log Whole Blood Lumi Ionized Aggregometer (Chrono-log, Haverton, Pa.) was used to provide a measurement of platelet aggregation in platelet-rich plasma. Briefly, platelet-rich plasma (PRP) was isolated from whole blood collected in 3.2% buffered trisodium citrate tubes (BD Vacutainer Systems, Franklin Lakes, N.J.); aptamer was added and incubated with the blood for 5 minutes before testing. After calibrating the instrument, 5 μL of agonist was added and transmission was measured for 10 minutes.

Ristocetin-Induced Platelet Aggregation (RIPA)

Ristocetin-induced platelet aggregation was performed using platelet rich plasma (PRP) from healthy volunteers. Clone VWF R9.3 or VWF R9.14 was mixed with 400 μL of PRP in a flat bottom glass tube; ristocetin (Helena Laboratories, TX) was added to a final concentration of 1.25 mg/mL. The PRP was stirred using a steel stir bar at 37° C. and turbidity was monitored as percent light transmitted for 10 minutes.

Collagen-Induced Platelet Aggregation (CIPA)

Collagen-induced platelet aggregation was performed using platelet rich plasma (PRP) from healthy volunteers. Clone VWF R9.3 or VWF R9.14 was mixed with 400 μL of PRP in a flat bottom glass tube and collagen was added to a final concentration of 2 μg/mL. The PRP was stirred using a steel stir bar at 37° C. and turbidity was monitored as percent light transmitted for 10 minutes.

ADP-Induced Platelet Aggregation (AIPA)

ADP-induced platelet aggregation was performed using platelet rich plasma (PRP) from healthy volunteers. Clone VWF R9.3 or VWF R9.14 was mixed with 400 μL of PRP in a flat bottom glass tube and ADP was added to a final concentration of 10 uM. The PRP was stirred using a steel stir bar at 37° C. and turbidity was monitored as percent light transmitted for 6 minutes.

Thrombin-Induced Platelet Aggregation (TIPA)

Thrombin-induced platelet aggregation was performed using platelet rich plasma (PRP) from healthy volunteers and SFLLRN peptide. Clone VWF R9.3 or VWF R9.14 was mixed with 400 μL of PRP in a flat bottom glass tube and SFLLRN was added to a final concentration of 2 nM. The PRP was stirred using a steel stir bar at 37° C. and turbidity was monitored as percent light transmitted for 6 minutes.

Results

Five Rounds SELEX Followed by Four Rounds of "Convergent" SELEX Yielded Aptamers that Bind to VWF with High Affinity.

To isolate RNA aptamers against VWF, a modified version of SELEX (Systematic Evolution of Ligands by EXponential enrichment) was performed. First, an RNA library containing 2'-fluoropyrimidines was incubated with total plasma proteins; the RNA ligands that bound to this proteome were recovered. Four additional rounds of SELEX were performed against the plasma proteome to generate a focused library that was highly enriched for RNA ligands that bound plasma proteins. Next, convergent SELEX (Layzer, Oligonucleotides 17:XX-XX (2007)) was performed to isolate those RNA aptamers from the focused library that specifically bound VWF. Such convergent SELEX progressed rapidly; the affinity of the round 4 pool of aptamers had a $K_d$ of 4.5 nM for VWF (FIG. 9A). Next, the identity of the individual aptamers was determined by cloning and sequencing. As shown in Table 3, two sequences dominated following round 4 of convergent SELEX against VWF (clones 9.3 and 9.4). These dominant clones, along with two less abundant clones (9.18 and 9.14), were chosen for further evaluation. To characterize the binding of these aptamers to VWF, nitrocellulose filter binding assays were performed. As shown in Table 3 and FIG. 1B, three of the four clones (9.3, 9.4 and 9.14) bound to VWF with high affinity ($K_d$<20 nM) (FIG. 1B). Thus, by performing 5 rounds of SELEX on the plasma proteome followed by 4 rounds of convergent SELEX against VWF using the plasma proteome focused library, aptamers were identified that bound to VWF with high affinity.

TABLE 3

P5V4 Aptamer Sequences

| Clone ID | Variable Region Sequence | SEQ ID NO: | Frequency (%) | Kd |
|---|---|---|---|---|
| VWF R9.3 | 5'-ATCGCGCTCTCCTGCTTAAGCAGCTATCAAATAGCCCACT-3' | 18 | 39 | 1.2 nM |
| VWF R9.4 | 5'-TATAGACCACAGCCTGAGATTAACCACCAACCCAGGACT-3' | 19 | 36 | 1.9 nM |
| VWF 89.18 | 5'-TGCTCCTTGGCCTTAGCCCTGGAACCATCAATCCTCTTCG-3' | 20 | 3 | 278 nM |
| VWF R9.14 | 5'-TGGACGAACTGCCCTCAGCTACTTTCATGTTGCTGACGCA-3' | 21 | 1 | 12 nM |
| VWF R9.90 | 5'-ACGNGTANACCTGCTACAATANCAGCCTAAATGGCCCACT-3' | 22 | 1 | N/D |
| VWF R9.66 | 5'-ATCCCTGCCAAACATACTTTCGCTTTGGCTAGGACTCCCT-3'|' | 23 | 3 | N/D |
| VWF R9.37 | 5'-GCACCCCCTCGACAACGACCCTGTGCCCCTCGATCGACCA-3' | 24 | 2 | N/D |
| VWF R9.54 | 5'-CCCATTACGGCTT-CCTTGTATTCTTGGACAAGCCGCGACT-3' | 25 | 2 | N/D |
| VWF R9.35 | 5'-ACCCTTGACAACAACCCTTCCTCACCAACCCCTCCCAAC-3' | 26 | 1 | N/D |
| VWF R9.81 | 5'-ATACCCTCGACAACGACCCTATTCGCATGACACCTCTGTG-3' | 27 | 1 | N/D |
| VWF R9.33 | 5'-ATGAATCCTCCTGTCGAACAACAGCTGTTTCAGCCCAACT-3' | 28 | 1 | N/D |
| VWF R9.93 | 5'-GACCGACTGATTCGCACCAGACCACGACGTTATGGCCCAA-3' | 29 | 1 | N/D |
| VWF R9.74 | 5'-GTCGACTTAGCCCCGTGCTCGGCGCTTCACAGTCGACTAT-3' | 30 | 1 | N/D |
| VWF R9.41 | 5'-CGAGATCACACTGCCCCAATAGCCACTGAACTAGCGCGCA-3' | 31 | 1 | N/D |
| VWF R9.46 | 5'-ACCATTCGCGAGCACAACGCTTTGTACTCAACACTCCACG-3' | 32 | 1 | N/D |
| VWF R9.49 | 5'-ACCGTTCAGAAATGACCCCACGCACATCCATCCCTGAGCT-3' | 33 | 1 | N/D |
| VWF R9.97 | 5'-ACGTGATCCTCGGACCCAGCATTGCATTATATGCGCCCCT-3' | 34 | 1 | N/D |
| VWF R9.95 | 5'-ACTCTCAGCCCATGTGCCTCAACCAAGGCACGGCTTGCTC-3' | 35 | 1 | N/D |
| VWF R9.62 | 5'-CACCCTTCACCCGAACCCTGCCC-ACG-ACCCCACACCCCGC-3' | 36 | 1 | N/D |
| VWF R9.57 | 5'-ATGACCAGCCCCTCGACAACGACCCTGCTGGCTCAACCGTT-3' | 37 | 1 | N/D |
| VWF 89.118 | 5'-GACCGCCGCNNCCGACCCNAGNNNTGCTGTGTNCGCTCCGCC-3' | 38 | 1 | N/D |

N/D-not determined

Clones VWF R9.3 and VWF R9.4 Bind to the VWF SPIII Domain but not to the VWF SPI Domain; Clone VWF R9.4 Binds to Both the VWF SPI and SPIII Domains.

To determine the specific binding domains of selected aptamer clones on VWF, studies were performed using VWF SPI and VWF SPIII domains. SP I and SP III are V8 protease fragments of VWF from the N-terminus of the protein. SPIII is 1365 residues in length (aa 1-1365) containing domains from D' mid-way through D4, including the A1 domain. SPI represents the C-terminal 455 residues of SPIII and contains mainly domain A3 and a part of domain D4 (FIG. 1D).

Clones VWF R9.3 and VWF R9.14 bound to the SPIII fragment but not to the SPI fragment (FIG. 1C and FIG. 1D). These results suggest that these aptamers bind proximal to the positively charged A1 domain of VWF. The A1 domain is mainly involved in platelet aggregation since it makes the contact with the GP Ibα subunit of platelet receptor GP Ib-IX- V. Clone VWF R9.4 bound to both SPI and SPIII domains, mapping its binding proximal to the VWF A3 domain (FIG. 1C).

Clones VWF R9.3 and VWF R9.14 but not VWF R9.4 Inhibited Platelet Function Measured by PFA-100.

To determine whether the isolated aptamers had any effect on platelet activity, they were evaluated for their ability to limit platelet-induced clot formation in a PFA-100 assay. The PFA-100 instrument uses small membranes coated with collagen/ADP or collagen/epinephrine to screen for the presence of platelet functional defects. As shown in FIG. 10A, VWF aptamers R9.3 and R9.14 inhibited platelet dependent clot formation completely in the PFA-100 assay (closing time>300 s) at a concentration of 1 μM. In contrast, VWF aptamer R9.4, while having a $K_d$ similar to R9.3 and R9.14, had no activity (FIG. 10A). Next, to determine the minimum effective dose of VWF aptamer R9.3 and VWF aptamer R9.14, a dose titration study was performed. As shown in FIG. 10B, both aptamers completely inhibited platelet function (CT>300 s) at concentrations greater than 40 nM in normal whole blood in the PFA-100 assay (FIG. 10B). Thus, at concentrations above 40 nM, these two aptamers inhibit platelet function to the level seen in patients with severe VWD.

Clones VWF R9.3 and VWF R9.14 Inhibited Platelet Aggregation Measured by RIPA but Not with CIPA, AIPA and TIPA.

To confirm these findings and to determine the specificity of the VWF aptamers, platelet aggregation studies were performed. First, an investigation was made of the effects of VWF aptamers R9.3 and R9.14 in a ristocetin induced platelet aggregation (RIPA) assay to determine if the aptamers inhibit platelet function by blocking VWF's ability to interact with GP Ib-IX-V. Ristocetin was used as a VWF antagonist because it binds specifically to VWF in platelet rich plasma (PRP) and assists in VWF-mediated platelet activation/aggregation through the GP Ib-IX-V receptor. Other antagonists (collagen, ADP and thrombin) that activate platelets through pathways that are not dependent on the VWF-GP Ib-IX-V interaction were also evaluated to determine if the aptamers had any inhibitory effect on these additional activation pathways. As shown in FIG. 10C, VWF aptamers R9.3 and R9.14 completely inhibited RIPA (at a concentration of 250 nM), illustrating that the aptamers can potently inhibit the VWF-GP Ib-IX-V interaction. In contrast, the aptamers had no effect in collagen, ADP or thrombin induced platelet aggregation (FIG. 10C). Thus, VWF aptamers R9.3 and R9.14 inhibit platelet function by specifically blocking VWF-GP Ib-IX-V-mediated platelet activation and aggregation.

Antidote Oligonucleotide 6 (AO6) can Reverse VWF R9.14 Binding to VWF to Background Levels.

Figure 11A:
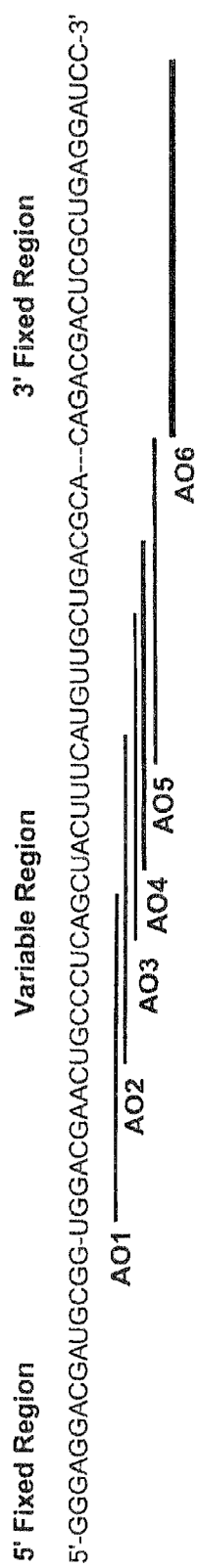
FIGS. 11A and 11B. Antidote oligonucleotides to R9.14 can inhibit aptamer binding to VWF.
Figure 11B:
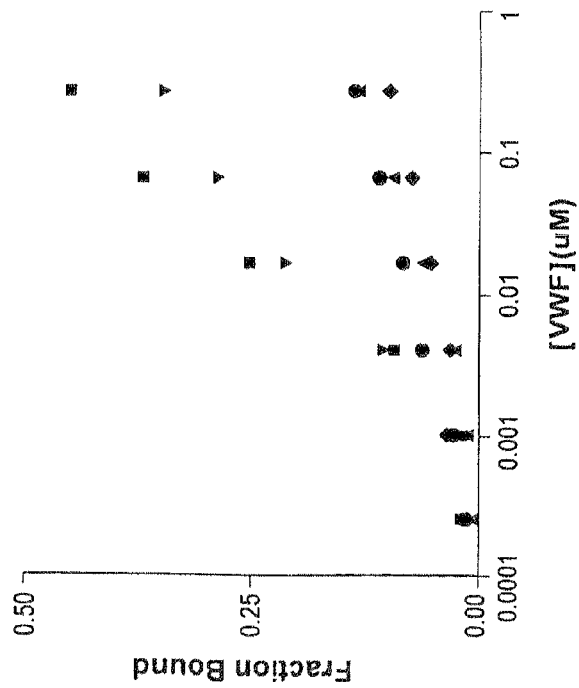

Six different antidote oligonucleotides (AO1-6) were designed to bind to VWF aptamer R9.14 through Watson-Crick base pairing rules (FIG. 11A). This strategy has been successfully employed to design an antidote to control the activity of an aptamer to factor IXa (Rusconi et al, Nature 419:90-94 (2002), Rusconi et al, Nat. Biotechnol. 22:1423-1428 (2004), Nimjee et al, Mol. Ther. 14:408-415 (2006)). To determine if the antidote oligonucleotides could inhibit aptamer binding to VWF, they were evaluated in a nitrocellulose filter binding assay. As shown in FIG. 11B, the most effective antidote for VWF aptamer. R9.14 is AO6. This antidote can reverse VWF aptamer R9.14's ability to bind VWF to background levels (FIG. 11B).

AO6 Can Reverse the Effects of VWF R9.14 Completely in a PFA-100 Assay.

Figure 12A:
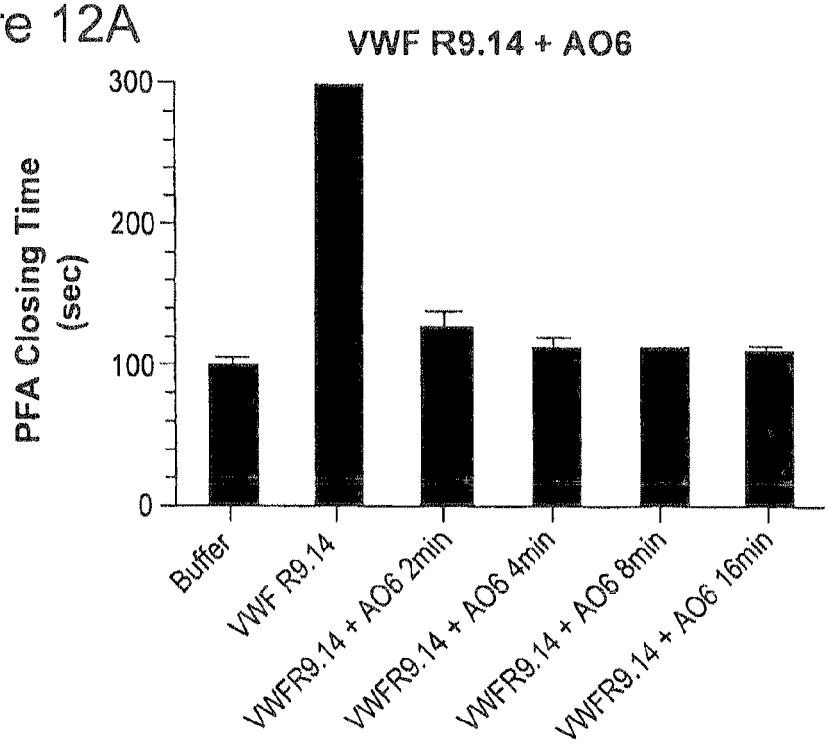
FIG. 12A-12C. Antidote oligonucleotides to aptamer VWF R9.14 can reverse aptamer function rapidly and for a prolonged period of time.

Since AO6 can reverse VWF aptamer 9.14 binding to VWF, it was next determined whether the antidote could also reverse the aptamer's activity in a whole blood clinical lab assay was tested. To that end, the ability of AO6 to inhibit VWF aptamer 9.14 was tested in a PFA-100 assay. As shown in FIG. 12A, the antidote can reverse the activity of the aptamer in a dose dependent manner. Moreover, the antidote is able to completely reverse the antiplatelet effects of the VWF aptamer R9.14 at a 40-fold excess of aptamer concentration. In contrast, a scrambled version of the antidote oligonucleotide (Scr AO6) had no effect on aptamer activity (FIG. 12A). Thus, antidote AO6 is able to restore platelet function in a whole blood assay back to normal levels, even in the presence of enough VWF aptamer 9.14 (40 nM) to impede platelet function to an extent consistent with VWD.

AO6 Can Quickly Reverse the Effects of VWF R9.14 for a Sustained Period of Time in a PFA-100 Assay.

Figure 12B:
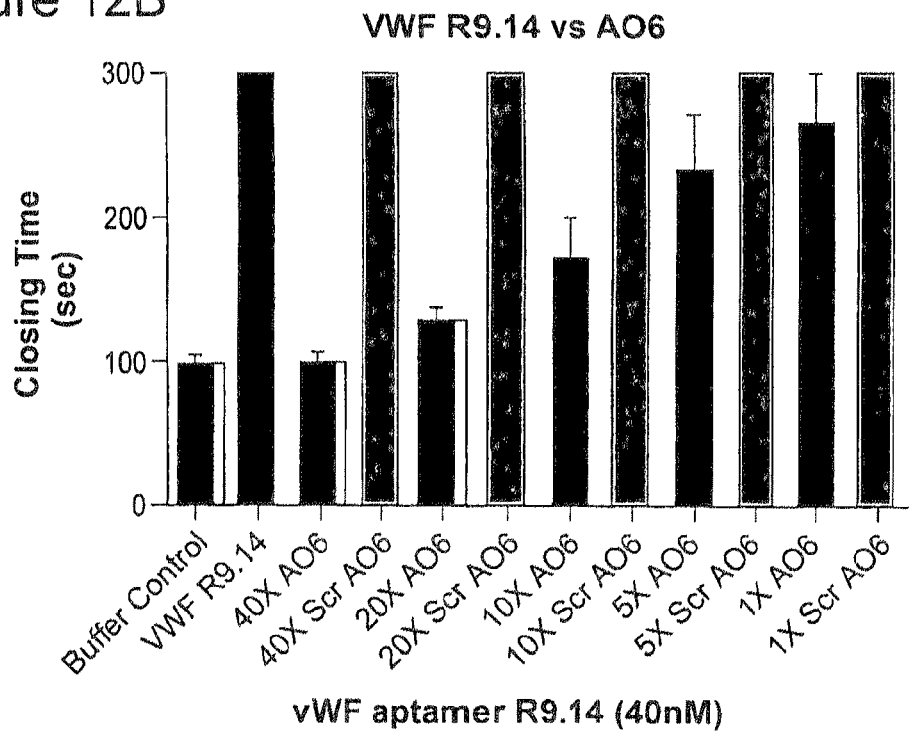
Figure 12C:
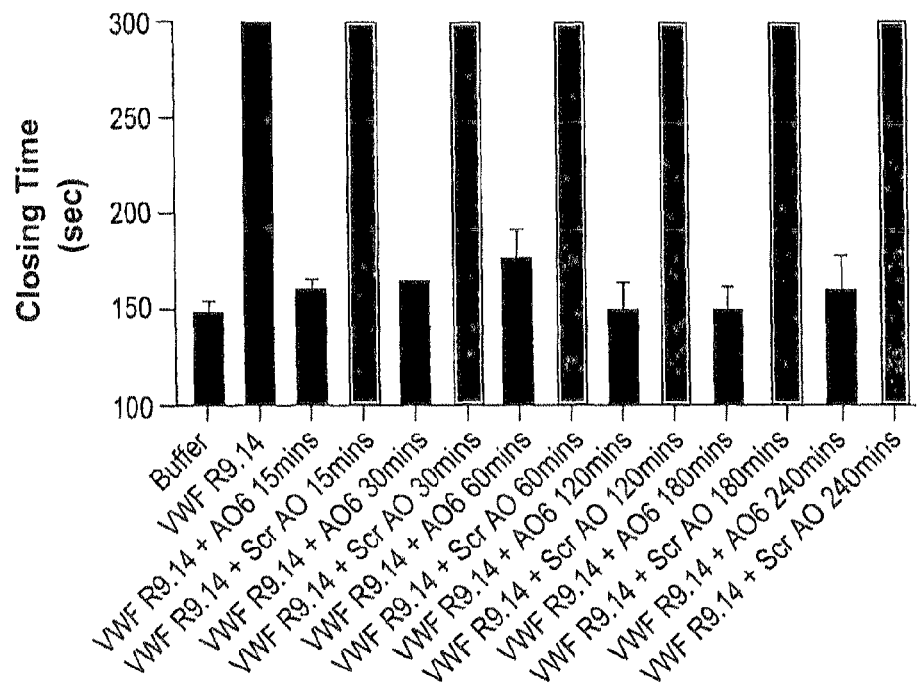

For such an antidote to be useful clinically, the antidote should be able to act quickly and for a prolonged period of time. To determine how rapidly AO6 could reverse the aptamer and how long such reversal is sustained, a time course assay was performed using the PFA-100. As shown in FIG. 12B, AO6 can rapidly reverse the effects of VWF aptamer R9.14 in less than 2 minutes. Moreover, once the antiplatelet activity is reversed, the antidote maintained its ability to sustainably inhibit the aptamer for greater than 4 hours (FIG. 12C). AO activity could not be tested for more than 4 hours due to platelet degradation over such time. These results demonstrate that AO6 can rapidly and durably reverse the effects of VWF aptamer R9.14.

In summary, aptamers are single-stranded nucleic acid molecules that can directly inhibit protein function by binding to their target with high affinity and specificity. To date, a number of proteins involved in coagulation have been targeted by aptamers, successfully yielding anticoagulant molecules with therapeutic potential (Rusconi et al, Thromb. Haemost. 84:841-848 (2000), Rusconi et al, Nature 419:90-94 (2002), Becker et al, Thromb. Haemost. 93:1014-1020 (2005), Nimjee et al, Trends Cardiovasc. Med. 15:41-45 (2005)). Aptamers represent an attractive class of therapeutic compounds for numerous reasons. They are relatively small (8 kDa to 15 kDa) synthetic compounds that possess high affinity and specificity for their target proteins (equilibrium dissociation constants ranging from 0.05-40 nM). Thus, they embody the affinity properties of monoclonal antibodies with the chemical production properties of small peptides. In addition, preclinical and clinical studies to date have shown that aptamers and compounds of similar composition are well tolerated, exhibit low or no immunogenicity, and are suitable for repeated administration as therapeutic compounds (Dyke et al, Circulation 114:2490-2497 (2006)). Moreover, bioavailability and clearance mechanisms of aptamers can be rationally altered by molecular modifications to the ligand (i.e. cholesterol or polyethylene glycol). Most importantly, it has been shown that antidote oligonucleotides can be rationally designed that negate the effect of aptamers in vitro and in vivo (Rusconi et al, Nature 419:90-94 (2002), Rusconi et al, Nat. Biotechnol. 22:1423-1428 (2004), Nimjee et al, Mol. Ther. 14:408-415 (2006)). Antiplatelet agents currently used in clinics can have a major bleeding side effect which can increase mortality and morbidity and significantly limit their use (Jackson et al, Nat. Rev. Drug. Discov. 2:775-789 (2003)). Using antidotes is the most effective and reliable way to control drug action and can reduce bleeding associated with current antiplatelet agent use in clinics, enhancing safety and reducing morbidity and mortality.

A technique termed "convergent" SELEX was used and a number of aptamers that bind to VWF with high affinity were isolated. Furthermore, it was shown that two of these clones inhibit VWF mediated platelet activation and aggregation in ex-vivo assays. Coincidentally, it has been demonstrated that both of these functional aptamers bind to the same region of VWF involved in platelet aggregation using VWF SPI and SPIII fragments. To test the characteristics of these aptamers in functional assays, a PFA-100 instrument was utilized. PFA-100 simulates platelet function in whole blood under high shear stress and is particularly sensitive to VWF defects (Harrison, Blood Rev. 19:111-123 (2005)). Both clone R9.3 and R9.14 completely inhibited platelet plug formation in PFA-100 at concentrations>40 nM (closing time>300s). Moreover, these aptamers were tested in ristocetin, ADP, thrombin (SFLLRN peptide) and collagen mediated platelet aggregation assays for pathway specificity. Both of these clones inhibited RIPA at >250 nM concentration but had no significant effect in other agonist mediated aggregation assays. These experiments show that both clone R9.3 and clone R9.14 bind VWF with high affinity and inhibit platelet aggregation through inhibition of GP Ib-IX-V-VWF interaction. This interaction is especially important around areas of high shear stress (i.e., stenosed arteries) and is a valid target for antiplatelet therapy.

Antidote control gives physicians added control over drug activity and provides a safer means for antiplatelet therapy. To further improve the safety of the lead molecule R9.14, an antidote oligonucleotide was rationally designed using the properties inherent to nucleic acids (Rusconi et al, Nature 419:90-94 (2002), Rusconi et al, Nat. Biotechnol. 22:1423-1428 (2004), Nimjee et al, Mol. Ther. 14:408-415 (2006)). Antidote oligonucleotides bind to their target aptamer through Watson-Crick base pairing, thus changing the aptamer's conformational shape and inhibiting binding to its target, therefore reversing its activity. Six different antidote oligonucleotides were designed and their activity tested in nitrocellulose filter binding assay. Antidote oligonucleotide 6 (AO6) was the most effective in inhibiting aptamer binding to VWF, completely reducing it to nonspecific, background levels. To test the effect of antidote AO6 on clone R9.14, the pair was tested in PFA-100. AO6 completely reverses the antiplatelet effect of R9.14 in less than 2 minutes and is effective for at least 4 hours. This aptamer-antidote pair can potentially give physicians a rapid, effective and continual way to regulate antiplatelet therapy.

EXAMPLE 4

Experimental Details
Synthesis of Aptamer Truncates and Antidote Oligonucleotides The antidote oligonucleotides and primers used in the truncation of the aptamer were synthesized and purified by IDT Inc (Coralville, Ind.). Software predicting RNA secondary structure (Mfold by M. Zuker) was used to aid in the design of truncates. Briefly, primers were designed to make progressively shorter DNA templates for aptamer molecules. T7 RNA polymerase was then used to transcribe RNA aptamers and tested each of these in binding assays.

Binding Assay

Dissociation constants ($K_d$) of each truncate were determined using double-filter nitrocellulose filter binding assays (Pergolizzi et al, Blood 108:862-869 (2006)). All binding studies were performed in binding buffer F (20 mM HEPES, pH 7.4, 150 mM NaCl, 2 mM $CaCl_2$, and 0.1% BSA) at 37° C. Human purified VWF (with factor VIII and factor VIII free) was purchased from Haematologic Technologies Inc. (Essex Junction, VT) and used in the double-filter nitrocellulose filter binding assay to determine the $K_d$ of individual clones. Briefly, RNA was dephosphorylated using bacterial alkaline phosphatase (Gibco BRL, Gaithberg, Md.) and end-labeled at the 5' end with T4 polynucleotide kinase (New England Biolabs, Beverly, Mass.) and [$\gamma^{32}$P] ATP (Amersham Pharmacia Biotech, Piscataway, N.J.). Direct binding was performed by incubating $^{32}$P—RNA with VWF in physiological buffer+1 mg/ml BSA at 37° C. for 5 min. The fraction of the nucleic acid-protein complex which bound to the nitrocellulose membrane was quantified with a phosphoimager (Molecular Dynamics, Sunnyvale, Calif.).

Non-specific binding of the radiolabeled nucleic acid was subtracted out of the binding such that only specific binding remained (Wong and Lohman, Proc. Natl. Acad. Sci. USA 90:5428-5432 (1993)).

Platelet Function Analysis

The Platelet Function Analyzer, PFA-100 (Dade Behring, Deerfield, Ill.), is a whole blood assay that measures platelet function in terms of clot formation time (Harrison, P., Blood Reviews 19:111-123 (2005)). It is highly sensitive to VWF levels. Briefly, whole blood (840 µl) was mixed with VWF aptamer in phosphate-buffered saline with magnesium and calcium (Sigma Aldrich, St. Louis, Mo.) and incubated for 5 minutes at room temperature. This mixture was then added to a collagen/ADP cartridge and tested for its closing time. The cartridge contains a microscopic aperture cut into a biologically active membrane at the end of a capillary. The whole blood is drawn through the aperture and the membrane is coated with collagen and adenosine diphosphate (ADP) or collagen and epinephrine which activate platelests. The activated platelet form a plug which occludes the aperture and stops blood flow. The time it takes for this to occur represents the closing time. The maximum closing time that the PFA-100 machine records is 300 seconds. The effect of the antidote oligonucleotides on the activity of the aptamer was measured by mixing whole blood with aptamer, incubating for 5 minutes followed by addition of antidote or negative control, and testing the mixture in the PFA-100.

Murine In vivo Studies

All in vivo experiments were approved by the Duke University Institutional Animal Care and Use Committee. All experiments were completed with the operator and the neuropathologist blinded to the treatment group.

Carotid Injury

Adult C57BL/6J mice (Jackson Laboratory, Bar Harbor, Me.) (18-24 g) were intubated and the left jugular vein was cannulated. Next, the right common carotid artery was exposed and a transonic flow probe (Transonic Systems Incorporated, Ithaca, N.Y.) was placed around the vessel. The blood flow was measured for 5 minutes to achieve a stable baseline followed by intravenous injection of negative control or aptamer Ch-9.14-T10. Carotid artery thrombosis was activated by 10% ferric chloride-soaked Whatmann paper as previously described (Konstantinides et al, Circulation 103:576-583 (2001)). The blood flow was then measured for 60 minutes. The time to occlusion was recorded. The animals were then sacrificed. The brain and common carotid arteries were harvested for analysis. The brain and carotid arteries were prepared on slides and stained with hematoxylin and eosin stains (Duke University Department of Pathology, Durham, N.C.) and reviewed by a neuropathologist (TJC), who was blinded to the treatment groups.

Tail Transaction

Adult mice (18-24 g) received Ch9.14T10 or saline by intraperitoneal (IP) injection. After 5 minutes, the mice were injected with saline or 10-fold molar excess of antidote oligonucleotide 1 (AO1). After 2 minutes, 2 mm of the distal tail was amputated and blood was collected for 15 minutes in 1 mL of phosphate-buffered saline at 37° C. Blood loss was determined by measuring the absorbance of saline at 550 nm and comparing the result to a standard curve constructed from known volumes of mouse blood as previously described (Fay et al, Blood 93:1825-1830 (1999)).

Data Analysis

All data is expressed as mean±standard deviation. All data was inputted into Graphpad Prism (Graphpad Software, La Jolla, Calif.). All statistical analysis was performed using Graphpad Prism or Graphpad Instat (Graphpad Software, La Jolla, Calif.).

Results

The VWF Aptamer Inhibits Thrombosis In Vivo

Figure 13:
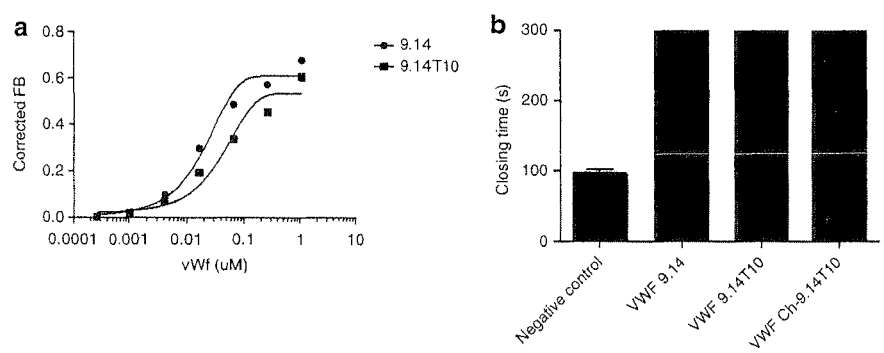
FIGS. 13A and 13B.

Previously described aptamer termed 9.14 (Table 4) binds and inhibits human VWF binding to human GP Ib-IX-V and prevents human platelet aggregation in vitro (Oney et al, Oligonucleotides 17:265-274 (2007)). To evaluate the ability of this aptamer to inhibit platelet function in animals, an attempt was first made to truncate and modify aptamer 9.14 to facilitate large scale synthesis of the oligonucleotide. Truncated versions of the aptamer were created and tested based on progressive deletion of nucleotides from the 3' end of the molecule (Table 4). It was determined that aptamer 9.14 could be truncated from 80 nucleotides to 60 nucleotides without significantly reducing its ability to bind VWF (dissociation constant ($K_d$) of 44 nM compared to 12 nM for the full length aptamer) (Oney et al, Oligonucleotides 17:265-274 (2007)) (FIG. 13A). Moreover, this truncated aptamer termed 9.14-T10 also retained its ability to inhibit platelet function as measured in a Platelet Function Analyzer (PFA-100) assay (FIG. 13B). Truncate 9.14-T10 also tolerated a cholesterol modification to the 5'-end of the aptamer (termed Ch-9.14-T10) to increase its circulating half-life in vivo (Rusconi et al, Nature Biotechnology 22:1423-1428 (2004)) without altering its ability to completely inhibit platelet aggregation (FIG. 13B).

TABLE 4

Sequences and binding properties of VWF aptamer truncates

| Aptamer | Length (nt) | Binding | Bmax (%) | Sequence |
|---|---|---|---|---|
| 9.14 | 80 | | 70 | GGGAGGACGATGCGGTGGACGAACTGCCCTCAGCTACTTTCATGTTGCTGACGCACAGACGACTCGCTGAGGATCCGAGA |
| 9.14 T1 | 77 | Similar | 72 | GGGAGGACGATGCGGTGGACGAACTGCCCTCAGCTACTTTCATGTTGCTGACGCACAGACGACTCGCTGAGGATCCG |
| 9.14 T2 | 72 | Decreased | 50 | GGGAGGACGATGCGGTGGACGAACTGCCCTCAGCTACTTTCATGTTGCTGACGCACAGACGACTCGCTGAGG |
| 9.14 T3 | 69 | Decreased | 50 | GGGAGGACGATGCGGTGGACGAACTGCCCTCAGCTACTTTCATGTTGCTGACGCACAGACGACTCGCTG |
| 9.14 T4 | 51 | No transcription | | GGGAGGCCTCAGCTACTTTCATGTTGCTGACGCACAGACGACTCGCTGAGG |
| 9.14 T5 | 66 | Decreased | 28 | GGGAGGACGATGCGGTGGACGAACTGCCCTCAGCTACTTTCATGTTGcrGACGCACAGACGACTCG |
| 9.14 T6 | 63 | Decreased | 36 | GGGAGGACGATGCGGTGGACGAACTGCCCTCAGCTACTTTCATGTTGCTGACGCACAGACAGC |
| 9.14 T7 | 59 | Decreased | 22 | GGGAGGACGATGCGGTGGACGAACTGCCCTCAGCTACTTTCATGTTGCTGACGCACAGA |
| 9.14 T8 | 66 | Similar | 67 | GGGAGGATGCGGTGGACGAACTGCCCTCAGCTACTTTCATGTTGCTGACGCACAGACGACTCGCTG |
| 9.14 T9 | 63 | No transcription | | GGGAGGCGGTGGACGAACTGCCCTCAGCTACTTTCATGTTGCTGACGCACAGACGACTCGCTG |
| 9.14 T10 | 60 | Similar | 61 | GGGAGGTGGACGAACTGCCCTCAGCTACTTTCATGTTGCTGACGCACAGACGACTCGCTG |
| 9.14 T11 | 57 | Decreased | 58 | GGGAGGADGAACTGCCCTCA.GCTACTTTCATGTTGCTGACGCACAGACGACTCGCiTG |
| 9.14 T12 | 54 | Decreased | 45 | GGGAGGAACTGCCCTCAGCTACTTTCATGTTGCTGACGCACAGACGACTCGCTG |
| 9.14 T13 | 51 | No transcription | | GGGAGGTGCCCTCAGCTACTTTCATGTTGCTGACGCACAGACGACTCGCTG |
| 9.14 T14 | 28 | No transcription | | GGGAGGTCAGCTACTTTCATGTTGCTGA |
| 9.14 T15 | 57 | No transcription | | GGGAGGTGGACGAACTGCCCTCAGCTACCATGTTGCTGACGCACAGACGACTCGCTG |
| 9.14 T16 | 54 | No transcription | | GGGAGGTGGACGAACTGCCCTCAGCTACGTTGCTGACGCACAGACGACTCGCTG |
| 9.14 T17 | 40 | No transcription | | GGGAGGTGGACGAACTGCCCTACGCACAGACGACTCGCTG |
| 9.14 T18 | 57 | Similar | 79 | GGGAGGTGGACGAACTGCCCTCTACTTTCATGTTGCTGACGCACAGACGACTCGCTG |
| 9.14 T19 | 54 | No transcription | | GGGAGGTGGACGAACTGCCCTCTTTCATGTTGCTGACGCACAGACGACTCGCTG |
| 9.14 T20 | 54 | No transcription | | GGGAGGTGGACGAACTGCCCTCTACTTTCATGTTGACGCACAGACGACTCGCTG |

Abbreviations: nt, nucleotide; VWF, von Willebrand factor.

Figure 14:
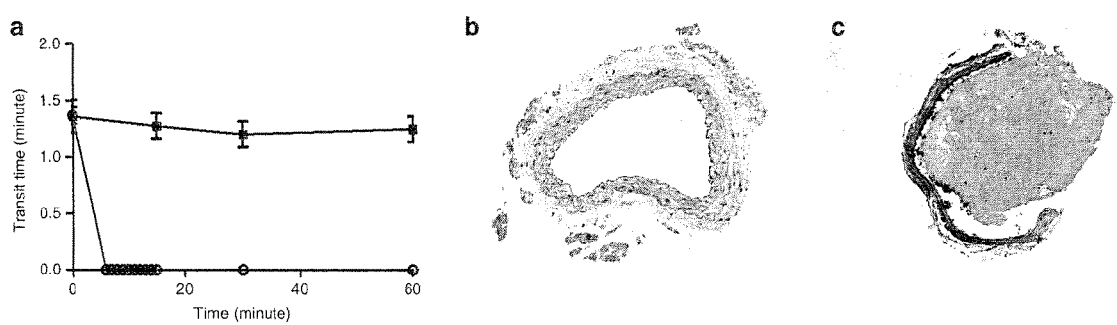
FIGS. 14A-14C.

To determine if the aptamer could inhibit platelet function in vivo, an evaluation was made of its ability to limit thrombosis in a ferric chloride-induced damage model of the common carotid artery in mice. After intubation, cannulation of the left jugular vein and placement of a flow probe around the right common carotid artery, each animal received an intravenous bolus injection of aptamer Ch-VWF 9.14 T10 (3 mg/kg, n=11) or phosphate-buffered saline (n=11). Next, Watmann paper (1 mm$^2$) soaked in 10% ferric chloride (370 mM) was placed on the carotid artery proximal to the flow probe and left on for 5 minutes to induce endothelial damage before being removed (Westrick et al, Arterioscler Thromb Vasc Biol 27:2079-2093 (2007)). The average time to thrombosis of the common carotid artery in the negative control group was approximately 10 minutes. By contrast the carotid arteries of all aptamer Ch-9.14 T10-treated mice remained patent until the end of the experiment (60 minutes) (p<0.0001 compared to the negative control group) (FIG. 14A). Moreover, no significant change in blood flow was observed in aptamer treated animals from the beginning of the experiment and for the entire 60 minutes of the experiment when the procedure was electively terminated (FIG. 14A).

Histological analysis of the carotid arteries of all the mice confirmed that vessels in the aptamer Ch-9.14-T10 treated animals were patent and devoid of thrombi (FIG. 14B). This observation was in stark contrast to all PBS-treated control mice, which had thrombi that had completely occluded their arteries (p<0.0001 of the Ch-9.14-T10-treated compared to PBS-treated controls) (FIG. 14C).

The VWF Aptamer Increases Bleeding from Surgically Challenged Animals

Figure 15:
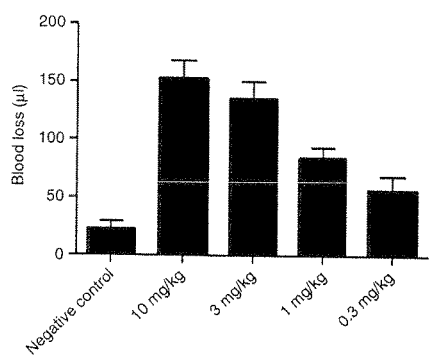
FIG. 15: VWF Aptamer Ch-9.14-T10 inhibits platelet plug formation in mice (n=5). Mice (18-24 g) were treated with 10, 3, 1 and 0.3 mg/kg of aptamer, then the distal 2 mm of their tails were clipped and blood loss measured. Animals treated with all doses of aptamer had significant blood loss when surgically challenged compared to animals not given the aptamer (p<0.0001). Y-axis represented blood loss in microliters (µl). Error bars represent the mean±SEM.

Once it was determined that aptamer Ch-9.14-T10 was a potent antithrombotic agent in vivo, its potential safety profile was evaluated. Therefore, animals that had received the aptamer were surgically challenged to determine the degree of bleeding. A murine tail-transection bleeding model was employed in which aptamer Ch-9.14-T10 was administered and 5 minutes later, the animal's tails were transected and the volume of blood lost over the next 15 minutes was measured. As anticipated from the bleeding diathesis described in VWF-knockout mice (Denis et al, Proc. Natl. Acad. Sci. USA 95:9524-9529 (1988), Pergolizzi et al, Blood 108:862-869 (2006)), mice treated with varying doses of aptamer Ch-9.14-T10 (10 mg/kg, 5 mg/kg, 3 mg/kg and 1 mg/kg, n=5 for each dose) exhibited significantly enhanced bleeding as compared with control animals (FIG. 15) (p<0.0001 comparing aptamer-treated mice at each dose to control animals). Moreover, this effect was dose-dependent and most of the aptamer-treated animals did not stop bleeding for the duration of the experiment, whereas all of the phosphate-buffered saline-treated animals formed a platelet plug at the tail transaction site and stopped bleeding within 15 minutes. These results demonstrate that, as expected for a potent platelet inhibitor, aptamer Ch-9.14-T10 can lead to significant blood loss in surgically-challenged animals. By contrast, no evidence of bleeding was observed in the brains of normal, adult mice that had been treated with aptamer Ch-9.14-T10 (3 mg/kg) for 1 hour and not surgically challenged. These results taken together suggest that the aptamer does not cause spontaneous bleeding, but can dramatically facilitate it at sites of vascular/tissue injury.

Therefore, after determining that aptamer Ch-9.14-T10 can prevent thrombosis but can also enhance bleeding, antidote molecules were developed that could be used to rapidly reverse the activity of aptamer Ch-9.14-T10 if needed.

Antidote Oligonucleotides and CDP Both Neutralize VWF Aptamer Activity In vitro.

Figure 16:
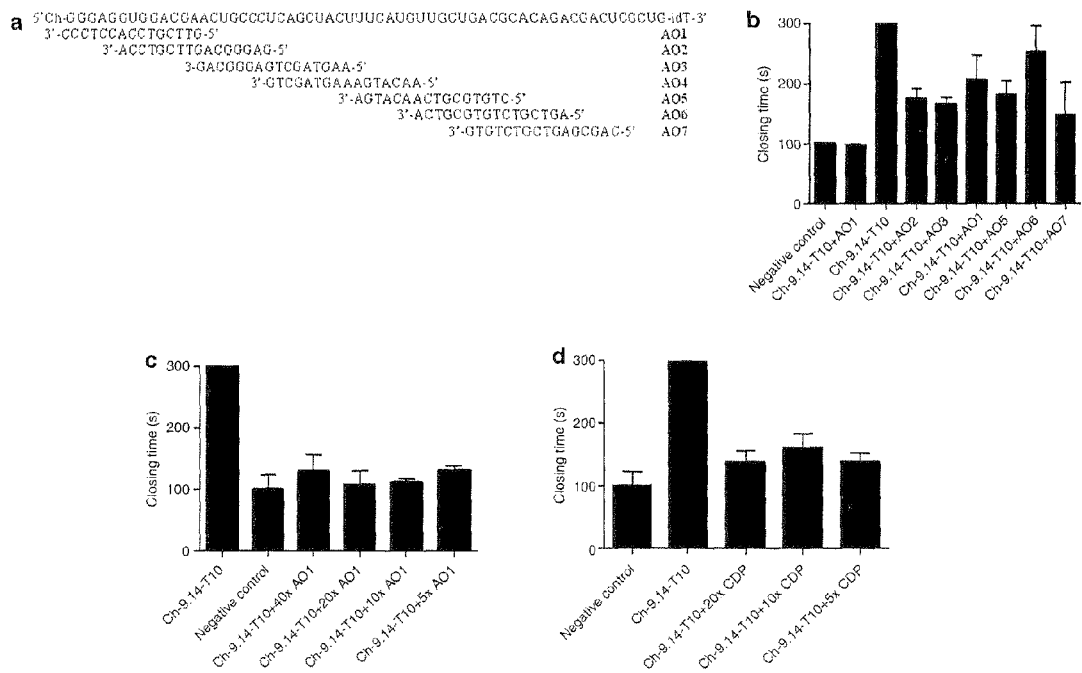
FIGS. 16A-16D: Antidotes for VWF aptamer Ch-9.14-T10.

Complementary antidote oligonucleotides were designed based on the sequence of aptamer Ch-9.14-T10 and base pairing rules (FIG. 16A). Initially, the antidotes were tested for their ability to reverse the aptamer's activity in a platelet function assay (PFA100) (FIG. 16B). In comparison to so the other antidote oligonucleotides (AOs), AO1 was the most potent reversal agent and it completely reversed the activity of aptamer Ch-9.14-T10 in 2 minutes (p=0.01 compared to other AO). AO1 was then tested at varying concentrations and it was found that the lowest concentration of AO1 (5-fold molar excess of AO1 over aptamer Ch-9.14-T10) completely is reversed aptamer activity in a PFA-100 assay. (FIG. 16C). These results demonstrate that VWF aptamer Ch-R9.14-T10 can be completely reversed by AO1 in vitro.

Beta-cyclodextrin-containing polycation (CDP) is a polymer that can bind to nucleic acid aptamers and inhibit their activity (Oney et al, Nature Medicine 15:1224-1228 (2009)). The ability of CDP to reverse the activity of Ch-9.14-T10 in the PFA100 was tested. As shown in FIG. 16D, it was observed that CDP could reverse the activity of the aptamer when added at a modest excess (>5-fold molar excess) over the aptamer.

After establishing that AO1 and CDP both inhibit the activity of Ch-9.14-110 in vitro, the activity of the aptamer and antidotes was tested in vivo.

Antidote Oligonucleotides and Universal Antidotes can Counteract the Activity of the VWF Aptamer in Mice and Thereby Limit Blood Loss in Surgically-Challenged Animals.

Figure 17:
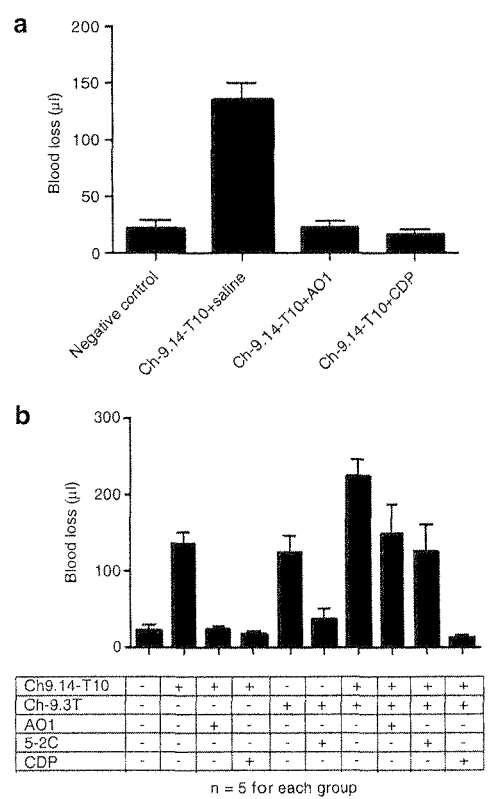
FIGS. 17A and 17B: Antidote control of VWF aptamer activity in vivo.

An evaluation was made of the ability of the antidote oligonucleotide, AO1, and the universal antidote, CDP, for their respective abilities to reverse aptamer Ch-R9.14-T10 activity in vivo. A murine tail transaction-bleeding model was used. Animals received aptamer Ch-R9.14-T10 (3 mg/kg) by intraperitoneal injection. Five minutes post aptamer administration, PBS, AO1, or CDP was injected into the tail vein at 10-fold molar excess over aptamer. The animals were then surgically challenged by tail transection and blood loss was monitored. Administration of AO1 or CDP completely reversed the enhanced bleeding provoked by aptamer Ch-9.14-T10 within two minutes (p<0.0001 between animals given or not given the antidote). Blood loss from the surgically challenged animals given the aptamer but not given the antidote was 135±34 µl. By contrast, blood loss from animals treated with the aptamer and then given AO1 or CDP was reduced to 23±12 µl and 17±10 µl, respectively. This amount of blood loss is not significantly different from animals surgically challenged but not administered the aptamer where blood loss was 22±16 µl (p>0.95 between no aptamer and aptamer plus AO1- and aptamer plus CDP-treated animals) (FIG. 17A).

Universal Antidotes can Counteract the Activity of Multiple Antithrombotic Aptamers In vivo while Antidote Oligonucleotides Only Control the Activities of Individual Aptamers Since both an antidote oligonucleotide (AO1) and a universal antidote (CDP) were able to rapidly reverse the activity of the VWF aptamer and prevent aptamer-dependent bleeding from surgically challenged animals, an investigation was made as to how these control agents may differ. It has been previously shown that an anti-factor IXa (FIXa) aptamer termed Ch9.3T inhibited coagulation FIXa activity in mice and caused increased bleeding and that enhanced bleeding could be controlled by administration of an antidote oligonucleotide termed 5-2C (Rusconi et al, Nature Biotechnology 22:1423-1428 (20004)). In this experiment, the object was to determine if a universal antidote could simultaneously neutralize both an anticoagulant and an antiplatelet aptamer. This question was of particular interest because, in many clinical settings; such as percutaneous coronary intervention where both anticoagulants and antiplatelet agents are employed in combination. Therefore, the anti-FIXa aptamer Ch9.3T (10 mg/kg) and the VWF aptamer Ch-R9.14-T10 (3 mg/kg) were administered to animals. Five minutes later, PBS or a 10-fold molar excess of an antidote oligonucleotide (AO1 or 5-2C) or the universal antidote CDP was administered. Then animals were surgically challenged by tail transection as previously described. Animals treated with the anticoagulant and antiplatelet aptamer combination, surgically challenged and not given an antidote (PBS control group) lost large amounts of blood (223±53 µl). As expected, this amount of blood loss was significantly greater than animals treated with the antiplatelet aptamer, Ch-R9.14-T10 alone (135±34 µl, p=0.014) (FIGS. 17A and 17B). Administration of AO1 or 5-2C decreased blood loss to a similar level (148±88 µl and 125±79 µl, respectively (p=0.72)), but remained elevated compared to animals that did not receive either aptamer (22±17 µl, (p=0.03)).

Administration of the universal antidote CDP to animals that had received both the anticoagulant and the antiplatelet aptamer, significantly reduced blood loss from surgically challenged animals (12±8 µl), a level markedly reduced compared to animals treated with both aptamers and given one of the matched antidote oligonucleotides (p=0.009 and p=0.01 compared to AO1 and 5-2C treated animals respectively). Moreover this amount of blood loss was not significantly different from mice that had not received an aptamer (p=0.27) (FIG. 17B).

In summary, these experiments demonstrate that the VWF aptamer Ch-9.14 T10 is a potent antiplatelet agent that can block thrombosis in vivo. As anticipated, administration of this potent platelet inhibitor enhances bleeding from animals that are surgically challenged. A matched antidote-oligonucleotide as well as a universal antidote can rapidly reverse the aptamer's antiplatelet activity and thereby limit surgically-induced bleeding.

Aptamer Ch-9.14-T10 was able to maintain vessel patency for greater than 1 hour in a murine $FeCl_3$ vascular injury thrombosis model and histopathologic analysis of the damaged carotid artery showed minimal evidence of platelet accumulation. It was previously determined that Ch-9.14-T10 binds to the A1 region of VWF and inhibits its interaction with platelet GP Ib (Oney et al, Oligonucleotides 17:265-274 (2007)), interfering with platelet adhesion to subendothelial collagen and impeding a key signal transduction pathway which subsequently leads to platelet aggregation through GP IIb/IIIa (Ruggeri, Z. M., Current Opinion in Hematology 10:142-149 (2003), Ruggeri et al, Blood 94:172-178 (1999)). Thus, it is believed that this mechanism of VWF inhibition is responsible for the potent anti-platelet effect observed in vivo.

While aptamer Ch-9.14-T10 exhibited potent in vivo antiplatelet activity, several antiplatelet agents have now been described with this ability (Cadroy et al, Blood 83:3218-3224 (1994), Jackson and Schoenwaelder, Nat. Rev. Drug Discov. 2:775-789 (2003)). However, this is the first description of an antiplatelet agent that can be neutralized rapidly and effectively by administration of an antidote molecule in vivo. Parenteral platelet inhibitors are used extensively by interventional cardiologists and radiologists and are now being used by neurosurgeons to aid in the surgical management of stroke and stent-assisted coiling of aneurysms (Gandhi et al, Curr Treat Options Cardiovasc Med 9:99-108 (2007), Nelson et al, Neurosurgery 59:S77-92; discussion 53 (2006), Bendok et al, Surg Neurol 62:304-311 (2004), N Engl J Med 339:436-443 (1998), Scarborough et al, Circulation 100:437-444 (1999), Topol et al, Lancet 353:227-231 (1999)). Both interventionalists and surgeons across vascular specialties are enthusiastic to use these types of drugs more extensively but are reluctant to do so because of concern for bleeding complications. Attenuating their pharmacodynamic activity in the event of bleeding requires blood product transfusion or recombinant clotting protease administration. Unfortunately, such procedures yield protracted and unknown quantitative inhibitory effects, are potentially prothrombotic and may be ineffective.

A number of agents targeting VWF, including mAbs and aptamers, have been shown to inhibit its activity and in turn, platelet function (Cosmi, B., Curr Opin Molec Therap 11:322-328 (2009), Diener et al, J. Thromb. Haemost 7:1155-1162 (2009), Wu et al, Blood 99:3623-3628 (2002), Yamamoto et al, Thromb Haemost 79:202-210 (1998), Cadroy et al, Blood 83:3218-3224 (1994), Gilbert et al, Circulation 116:2678-2686 (2007), Mayr et al, Transfusion 50:1079-1087 (2010), Spiel et al, Platelets 20:334-340 (2009)). However, antidotes have not been described for any of these drugs, limiting their overall clinical utility in surgical settings. The VWF aptamer and its antidotes, including universal antidotes such as CDP represent the first controllable anti-platelet agent and can provide clinicians with much needed options in surgical settings where thrombotic and hemorrhagic risk coexist.

* * *

All documents and other information sources cited above are hereby incorporated in their entirety by reference.

What is claimed is:

1. A nucleic acid aptamer that binds to von Willebrand Factor (VWF) with high affinity and inhibits platelet function in vivo, wherein the aptamer is SEQ ID NO: 56 and includes a 3' or 5' modification, wherein said modification confers improved in vivo stability and/or delivery of the nucleic acid aptamer.

2. The aptamer according to claim 1 wherein said aptamer inhibits binding of VWF to GP 1b-IX-V.

3. The nucleic acid aptamer of claim 1, wherein the modification is selected from a cap, PEG or cholesterol modification.

4. The nucleic acid aptamer of claim 3, wherein said modification is a 5' cholesterol modification.

5. A composition comprising said aptamer according to claim 1 and a carrier.

6. A method of inhibiting platelet aggregation in a subject comprising contacting VWF with an amount of said aptamer according to claim 1 so that said inhibition is affected.

* * * * *